United States Patent
Du

(10) Patent No.: US 10,578,630 B2
(45) Date of Patent: Mar. 3, 2020

(54) AUTOMATED IDENTIFICATION OF ASSAY AREAS IN A MICROFLUIDIC DEVICE AND DETECTION OF ASSAY POSITIVE AREAS BASED ON RATE OF CHANGE OF IMAGE LIGHT INTENSITY

(71) Applicant: Berkeley Lights, Inc., Emeryville, CA (US)

(72) Inventor: Fenglei Du, Fremont, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 857 days.

(21) Appl. No.: 14/964,025

(22) Filed: Dec. 9, 2015

(65) Prior Publication Data

US 2016/0160259 A1 Jun. 9, 2016

Related U.S. Application Data

(60) Provisional application No. 62/259,511, filed on Nov. 24, 2015, provisional application No. 62/089,229, filed on Dec. 9, 2014.

(51) Int. Cl.

| | |
|---|---|
| G01N 35/00 | (2006.01) |
| G01N 21/84 | (2006.01) |
| G01N 21/64 | (2006.01) |
| G01N 21/75 | (2006.01) |
| B01L 3/00 | (2006.01) |
| B01L 7/00 | (2006.01) |

(52) U.S. Cl.
CPC ......... *G01N 35/00* (2013.01); *G01N 21/6458* (2013.01); *G01N 21/75* (2013.01); *G01N 21/8483* (2013.01); *B01L 3/502792* (2013.01); *B01L 7/00* (2013.01); *B01L 2200/0668* (2013.01); *B01L 2200/147* (2013.01); *B01L 2200/148* (2013.01); *B01L 2300/024* (2013.01); *B01L 2300/0883* (2013.01); *B01L 2300/1822* (2013.01); *B01L 2400/0415* (2013.01); *B01L 2400/0427* (2013.01); *B01L 2400/0472* (2013.01); *G01N 2021/752* (2013.01); *G01N 2021/755* (2013.01); *G01N 2021/757* (2013.01); *G01N 2201/0635* (2013.01)

(58) Field of Classification Search
None
See application file for complete search history.

(56) References Cited

U.S. PATENT DOCUMENTS

| | | | |
|---|---|---|---|
| 6,294,063 B1 | 9/2001 | Becker | |
| 6,541,213 B1 | 4/2003 | Weigl | |
| 6,942,776 B2 | 9/2005 | Medoro | |
| 7,090,759 B1 | 8/2006 | Seul | |
| 2003/0008364 A1 | 1/2003 | Wang | |
| 2003/0224528 A1 | 12/2003 | Chiou | |
| 2004/0072278 A1 | 4/2004 | Chou | |
| 2004/0191789 A1 | 9/2004 | Manaresi et al. | |
| 2005/0112548 A1 | 5/2005 | Segawa et al. | |
| 2005/0175981 A1 | 8/2005 | Voldman et al. | |
| 2006/0091015 A1 | 5/2006 | Lau | |
| 2007/0095669 A1 | 5/2007 | Lau et al. | |
| 2007/0183934 A1 | 8/2007 | Diercks et al. | |
| 2008/0013092 A1 | 1/2008 | Maltezos et al. | |
| 2008/0014575 A1 | 1/2008 | Nelson | |
| 2008/0302732 A1 | 12/2008 | Soh et al. | |
| 2009/0075828 A1 | 3/2009 | Fisher et al. | |
| 2009/0170186 A1 | 7/2009 | Wu et al. | |
| 2009/0324089 A1 | 12/2009 | Morita | |
| 2010/0003666 A1 | 1/2010 | Lee et al. | |
| 2010/0101960 A1 | 4/2010 | Ohta et al. | |
| 2011/0117634 A1 | 5/2011 | Halamish et al. | |
| 2012/0024708 A1 | 2/2012 | Chiou et al. | |
| 2012/0118740 A1 | 5/2012 | Garcia et al. | |
| 2012/0148140 A1 | 6/2012 | Di Carlo et al. | |
| 2012/0149128 A1 | 6/2012 | Manneh | |
| 2012/0325665 A1 | 12/2012 | Chiou et al. | |
| 2013/0109030 A1 | 5/2013 | Hardemam et al. | |
| 2013/0118905 A1 | 5/2013 | Morimoto et al. | |
| 2013/0171628 A1 | 7/2013 | Di Carlo et al. | |

(Continued)

FOREIGN PATENT DOCUMENTS

| | | |
|---|---|---|
| WO | 20080131048 | 10/2008 |
| WO | 2010147078 | 12/2010 |
| WO | 2004089810 | 10/2014 |

OTHER PUBLICATIONS

Chiou et al., Massively Parallel Manipulation of Single Cells and Microparticles Using Optical Images, Nature 436:370-73 (2005).
Dishinger et al., Serial Immunoassays in Parallel on a Microfluidic Chip for Monitoring Hormone Secretion from Living Cells, Analytical Chemistry 79;947-54 (2007).

(Continued)

*Primary Examiner* — G Steven Vanni
(74) *Attorney, Agent, or Firm* — Kenneth E. Horton; Kirton McConkie

(57) ABSTRACT

Methods are provided for the automated detection of assay-positive assay areas in a microfluidic device. When assays are performed in a microfluidic device, the configuration of the microfluidic circuit and its constituent circuit elements can determine where the reagents/analytes used in the assay can be located within the microfluidic circuit. Methods are provided for automatic identification of the size and shape of the assay areas based on a number of parameters which may include type of assay involved, shape and dimensions of microfluidic circuit elements, velocity and physical characteristics of the fluidic medium within the microfluidic circuit, physical/chemical properties of the analytes/reagents, and/or the number of cells being assayed.

29 Claims, 12 Drawing Sheets

(56) References Cited

U.S. PATENT DOCUMENTS

| | | |
|---|---|---|
| 2013/0190212 A1 | 7/2013 | Handique et al. |
| 2013/0204076 A1 | 8/2013 | Han et al. |
| 2014/0017709 A1 | 1/2014 | Lowe et al. |
| 2014/0116881 A1 | 5/2014 | Chapman et al. |
| 2014/0371097 A1 | 12/2014 | Conti et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2016/0171686 A1 | 6/2016 | Du et al. |
| 2016/0193604 A1 | 7/2016 | McFarland et al. |
| 2016/0252495 A1 | 9/2016 | Ricicova et al. |

OTHER PUBLICATIONS

Jongpaiboonkit et al., An Adaptable Hydrogel Array Format for 3-Dimensional Cell Culture and Analysis, Biomaterials 29:3346-3356 (2008).

Valley et al., Optoelectronic Tweezers as a Tool for Parallel Single-Cell Manipulation and Stimulation, IEEE Transactions on Biomedical Circuits and Systems 3(6):424-30 (2009).

Hsu et al., Sorting of Differentiated Neurons using Phototransistor-based Optoelectronic Tweezers for Cell Replacement Therapy of Neurodegenerative Diseases, IEEE Conference on Transducers (Jun. 21-25, 2009).

Zhang et al., Controlled Aspiration and Positioning of Biological Cells in a Micropipette, IEEE Transactions on Biomedical Engineering, vol. 59, No. 4, pp. 1032-1040 (2012).

International Search Report and Written Opinion for PCT Application Serial No. PCT/US2015/064718 (dated Mar. 9, 2016), 12 pages.

AUTOMATED IDENTIFICATION OF ASSAY AREAS IN A MICROFLUIDIC DEVICE AND DETECTION OF ASSAY POSITIVE AREAS BASED ON RATE OF CHANGE OF IMAGE LIGHT INTENSITY

CROSS REFERENCE TO RELATED APPLICATION(S)

This application is a non-provisional of, and thus claims the benefit of and/or priority to, U.S. provisional patent application Ser. No. 62/089,229, filed on Dec. 9, 2014 and U.S. provisional patent application Ser. No. 62/259,511, filed on Nov. 24, 2015, the entire contents of which are incorporated herein by reference.

FIELD

The present invention generally relates to methods for detecting the results of an assay within a microfluidic device. In particular, the methods can include steps for automatically selecting specific regions within the microfluidic device for detection of assay results.

BACKGROUND

As the field of microfluidics continues to progress, microfluidic devices have become convenient platforms for processing and manipulating micro-objects such as biological cells. Some embodiments of the present invention are directed to methods and devices for the automated use of microfluidic devices.

SUMMARY OF THE INVENTION

In a first aspect, the present invention relates to an automated method of detecting an assay-positive assay area within a microfluidic device comprising one or more circuit elements. The automated method comprises collecting a set of digital images $I_i$ (i=1 to n) of an automatically-identified assay area $AA_x$, wherein the automatically-identified assay area $AA_x$, is identified based, at least in part, on the dimensions of the one or more circuit elements. The automated method further comprises calculating a rate of change $\Delta_x$ over the course of all or part of the assay based on the set of digital images $I_i$ of the automatically-identified assay area $AA_x$. The automated method further comprises comparing the rate of change $\Delta_x$ to a threshold value $\Delta°$ and determining that the automatically-identified assay region $AA_x$ is assay-positive if $\Delta_x$ is greater than $\Delta°$.

In various embodiments of the present invention, the microfluidic device comprises a channel and the automated method comprises identifying the automatically-identified assay area $AA_x$, is based, at least in part, on the dimensions of the channel. In some embodiments, the dimensions of the channel include a width of the channel.

In various embodiments of the present invention, the microfluidic device comprises a sequestration pen and the automated method comprises identifying the automatically-identified assay area $AA_x$, is based, at least in part, on the dimensions of the sequestration pen. In some embodiments, the dimensions of the sequestration pen include a width of the sequestration pen. In some embodiments, the dimensions of the sequestration pen include a length of the sequestration pen.

In various embodiments, the automated method comprises identifying the automatically-identifying assay area $AA_x$, based on the position of a cell within the sequestration pen. In some embodiments, the automated method further comprises detecting the position of the cell within the sequestration pen.

In various embodiments of the present invention, the automated method comprises identifying the automatically-identified assay area $AA_x$, is based, at least in part, on whether the assay is a secretion assay.

In various embodiments of the present invention, the automated method comprises identifying the automatically-identified assay area $AA_x$, based, at least in part, based, at least in part, on the properties of a reagent or analyte used in the assay. In some embodiments, the automated method comprises identifying the automatically-identified assay area $AA_x$, is based, at least in part, on the location of a reagent or analyte that has been affixed to a portion of the sequestration pen or a portion of the channel. In some embodiments, the automated method further comprises affixing the reagent or analyte to the portion of the sequestration pen by using structured light to actuate solidification of a light-actuated polymer network.

In various embodiments of the present invention, the automated method comprises collecting digital images of the set of digital images $I_i$ (i=1 to n) periodically. In some embodiments, the period for collecting digital images of the set of digital images $I_i$ (i=1 to n) is once every 3 to 5 minutes.

In various embodiments of the present invention, the set of digital images $I_i$ (i=1 to n) comprises a set of pixels $P_{i,j}$ and the automated method further comprises determining a light intensity value $L_{i,j}$ of the set of pixels $P_{i,j}$ or a subset of the set of pixels $P_{i,j}$. In some embodiments, determining a light intensity value $L_{i,j}$ for a pixel $P_{i,j}$ comprises subtracting a background level of light intensity from the observed level of light intensity ($L_{i,j}$(observed)−$L_{i,j}$(background)). In some embodiments, $L_{i,j}$(background) is the light intensity value measured for the same pixel $P_j$ at the beginning of the assay (t=0) or just prior to the start of the assay. In some embodiments, $L_{i,j}$(background) is a light intensity value $L_{ctrl}$ observed for a control area.

In various embodiments of the present invention, the rate of change $\Delta_x$ is a vector or other mathematical expression that represents the rate of change of two or more of the parameters selected from the group consisting of $L_{i,avg}$, $\sigma_i$, $L_{i,min}$, and $L_{i,max}$.

In various embodiments of the present invention, the threshold $\Delta°$ is based on the $\Delta_{avg}$ and the standard deviation $\sigma°$ for the rates of change $\Delta_x$ corresponding to k different assay areas $AA_x$ (x=1 to k). IN some embodiments, the threshold $\Delta°$ is equal to $\Delta_{avg}+1.6\sigma°$.

In a second aspect, the present invention relates to a machine readable storage device for storing non-transitory machine readable instructions for carrying out the automated method of detecting an assay-positive assay area within a microfluidic device comprising one or more circuit elements and various embodiments thereof.

In a third aspect, the present invention relates to an automated method of detecting a quantity of an analyte within a microfluidic device comprising one or more circuit elements. The automated method comprises collecting a set of digital images $I_i$ (i=1 to n) of an automatically-identified assay area $AA_x$, wherein the automatically-identified assay area $AA_x$, is identified based, at least in part, on the dimensions of the one or more circuit elements. The automated method further comprises calculating a rate of change $\Delta_x$ over the course of all or part of the assay based on the set of digital images $I_i$ of the automatically-identified assay area $AA_x$. The automated method further comprises determining a quantity of an analyte associated with the rate of change $\Delta_x$ based on a calibration curve, wherein the calibration curve comprises one or more rates of change $\Delta_x$ corresponding to known concentrations of the analyte.

In various embodiments, the automated method further comprising determining the one or more rates of change $\Delta_x$ corresponding to known concentrations of the analyte. In some embodiments, the automated method further comprises collecting one or more sets of digital images $I_i$ (i=1 to n) of one or more automatically-identified assay areas $AA_x$ associated with known concentrations of the analyte; and calculating the one or more rate of change $\Delta_x$ over the course of all or part of the assay based on the one or more set of digital images $I_i$ of the automatically-identified assay area $AA_y$.

In a fourth aspect, the present invention relates to a machine readable storage device for storing non-transitory machine readable instructions for carrying out the automated method of detecting a quantity of an analyte within a microfluidic device comprising one or more circuit elements and various embodiments thereof.

DETAILED DESCRIPTION OF EXEMPLARY EMBODIMENTS

Figure 1:
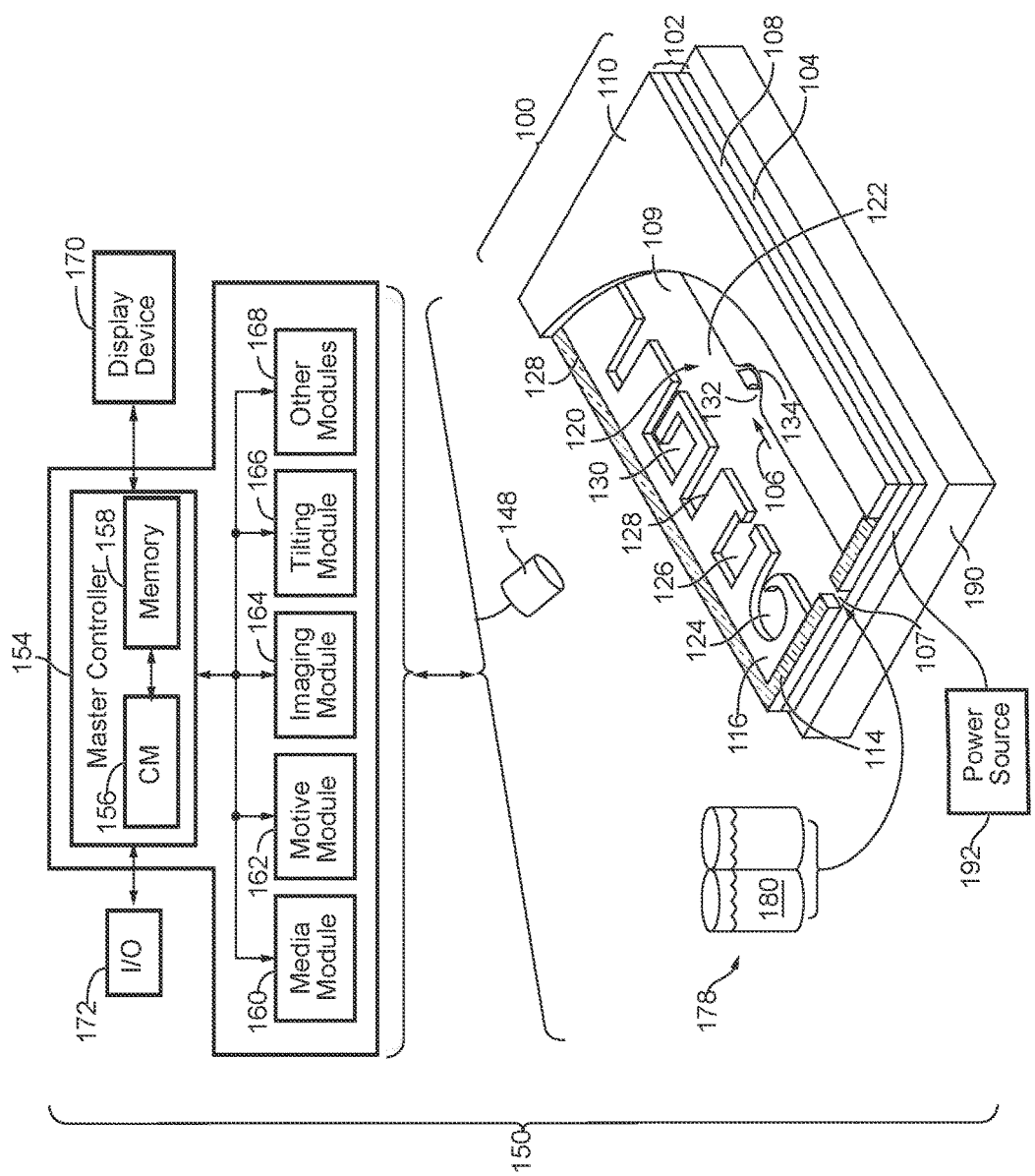
FIG. 1 illustrates an example of a system for use with a microfluidic device and associated control equipment according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements.

Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one. As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and collected in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cell, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices.

FIG. 1 illustrates an example of a microfluidic device 100 and a system 150 which can be used in the practice of the present invention. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic sequestration pens 124, 126, 128, and 130, each having one or more openings in fluidic communication with flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1, the microfluidic circuit 120 is defined by an enclosure 102. Although the enclosure 102 can be physically structured in different configurations, in the example shown in FIG. 1 the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow channels, chambers, pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise the frame 114 and microfluidic circuit material 116 can be separate structures as shown in FIG. 1 or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3, the imaging device 194 may further include a microscope (or an optical train), which may or may not include an eyepiece.

System 150 further comprises a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100.

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 2A and 2B, the enclosure 102 can comprise a dielectrophoresis (DEP), optoelectronic tweezers (OET) and/or opto-electrowetting (OEW) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. In some instances, pens 124, 126, 128, 130 are configured to physically corral one or more micro-objects within the microfluidic circuit 120. Sequestration pens in accordance with the present invention can comprise various shapes, surfaces and features that are optimized for use with DEP, OET, OEW, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful in performing assays (e.g. culturing and retaining micro-objects used in assays). In some embodiments, the microfluidic circuit 120 comprises a plurality of identical microfluidic sequestration pens. In some embodiments, the microfluidic circuit 120 comprises a plurality of microfluidic sequestration pens, wherein two or more of the sequestration pens comprise differing structures and/or features. For example, the sequestration pens can provide differing benefits with regard to performing assays.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens are configured (e.g., relative to a channel 122) such that they can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the teachings of the instant invention. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the teachings of the instant invention.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 2A:
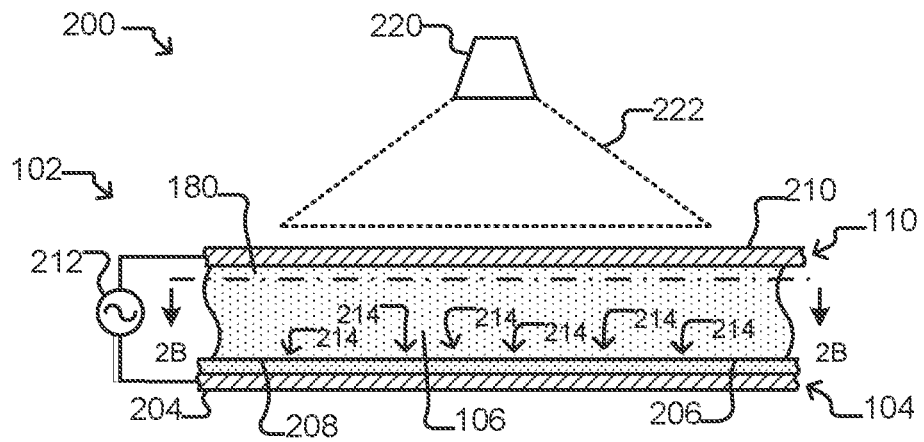
FIGS. 2A and 2B illustrate a microfluidic device according to some embodiments of the invention.

FIGS. 2A-2F illustrates various embodiments of microfluidic devices that can be used in the practice of the present invention. FIG. 2A depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Motive Microfluidic Device Configurations.

As described above, the control and monitoring equipment of the system can comprise a motive module 162 for selecting and moving objects, such as micro-objects or droplets, in the microfluidic circuit of a microfluidic device.

The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 2B:
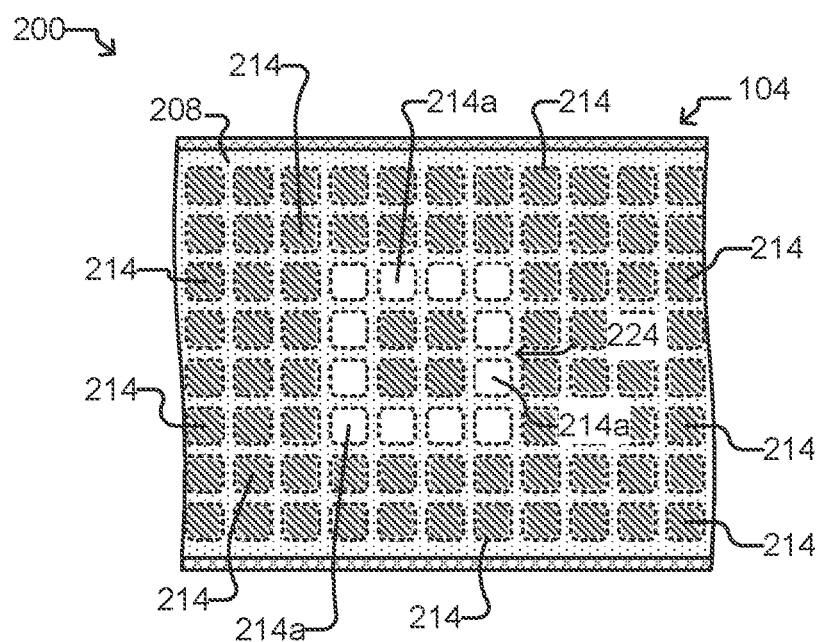

One example of a microfluidic device 200 comprising a DEP configuration is illustrated in FIGS. 2A and 2B. While for purposes of simplicity FIGS. 2A and 2B show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 2A, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 2A and 2B can have an optically-actuated DEP configuration. Accordingly, changing patterns of light 222 from the light source 220, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 2B, a light pattern 222 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 222 projected from a light source 220 into the microfluidic device 200. Whether the DEP forces attract or repel nearby micro-objects can depend on such parameters as the frequency of the power source 212 and the dielectric properties of the medium 180 and/or micro-objects (not shown).

The square pattern 224 of illuminated DEP electrode regions 214a illustrated in FIG. 2B is an example only. Any pattern of the DEP electrode regions 214 can be illuminated (and thereby activated) by the pattern of light 222 projected into the device 200, and the pattern of illuminated/activated DEP electrode regions 214 can be repeatedly changed by changing or moving the light pattern 222.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*(the number of hydrogen atoms)/(the total number of hydrogen and silicon atoms)). The layer of a-Si:H can have a thickness of about 500 nm to about 2.0 µm. In such embodiments, the DEP electrode regions 214 can be created anywhere and in any pattern on the inner surface 208 of the electrode activation substrate 208, in accordance with the light pattern 222. The number and pattern of the DEP electrode regions 214 thus need not be fixed, but can correspond to the light pattern 222. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 222. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 222, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 222.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 220 can alternatively be used to illuminate the enclosure 102 from below.

With the microfluidic device 200 of FIGS. 2A-2B having a DEP configuration, the motive module 162 can select a micro-object (not shown) in the medium 180 in the region/chamber 202 by projecting a light pattern 222 into the device 200 to activate a first set of one or more DEP electrodes at DEP electrode regions 214a of the inner surface 208 of the electrode activation substrate 206 in a pattern (e.g., square pattern 224) that surrounds and captures the micro-object. The motive module 162 can then move the captured micro-object by moving the light pattern 222 relative to the device 200 to activate a second set of one or more DEP electrodes at DEP electrode regions 214. Alternatively, the device 200 can be moved relative to the light pattern 222.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 224), one or more micro-objects in region/chamber 202 can be trapped and moved within the region/chamber 202. The motive module 162 in FIG. 1 can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker, such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*(the number of hydrogen atoms)/(the total number of hydrogen and silicon atoms)). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 222 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 222 (or moving microfluidic device 200 relative to the light source 220) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1 can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration Pens.

Figure 2C:
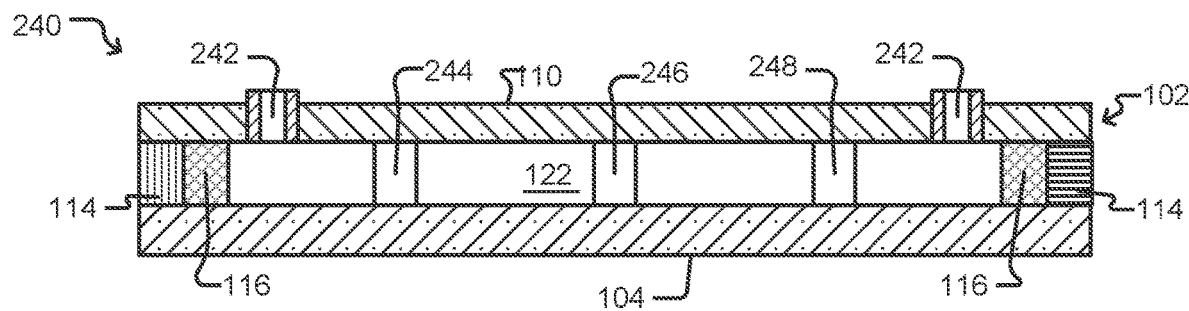
FIGS. 2C and 2D illustrate sequestration pens according to some embodiments of the invention.
Figure 2D:
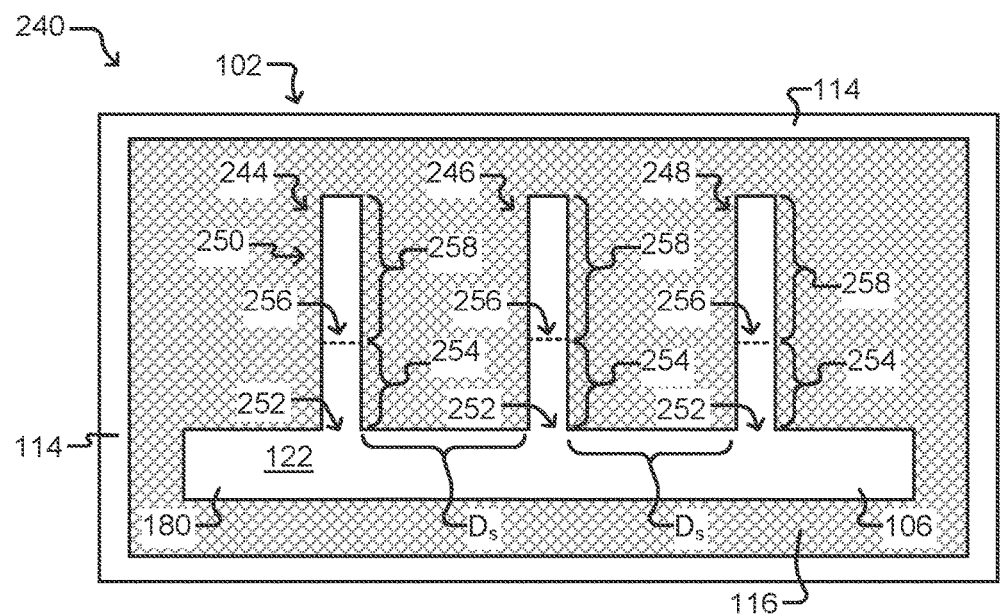

Non-limiting examples of generic sequestration pens 244, 246, and 248 are shown within the microfluidic device 240 depicted in FIGS. 2C and 2D. Each sequestration pen 244, 246, and 248 can comprise an isolation structure 250 defining an isolation region 258 and a connection region 254 fluidically connecting the isolation region 258 to a channel 122. The connection region 254 can comprise a proximal opening 252 to the channel 122 and a distal opening 256 to the isolation region 258. The connection region 254 can be configured so that the maximum penetration depth of a flow of a fluidic medium (not shown) flowing from the channel 122 into the sequestration pen 244, 246, 248 does not extend into the isolation region 258. Thus, due to the connection region 254, a micro-object (not shown) or other material (not shown) disposed in an isolation region 258 of a sequestration pen 244, 246, 248 can thus be isolated from, and not substantially affected by, a flow of medium 180 in the channel 122.

The channel 122 can thus be an example of a swept region, and the isolation regions 258 of the sequestration pens 244, 246, 248 can be examples of unswept regions. As noted, the channel 122 and sequestration pens 244, 246, 248 can be configured to contain one or more fluidic media 180. In the example shown in FIGS. 2C-2D, the ports 242 are connected to the channel 122 and allow a fluidic medium 180 to be introduced into or removed from the microfluidic device 240. Once the microfluidic device 240 contains the fluidic medium 180, the flow 260 of fluidic medium 180 in the channel 122 can be selectively generated and stopped. For example, as shown, the ports 242 can be disposed at different locations (e.g., opposite ends) of the channel 122, and a flow 260 of medium can be created from one port 242 functioning as an inlet to another port 242 functioning as an outlet.

Figure 2E:
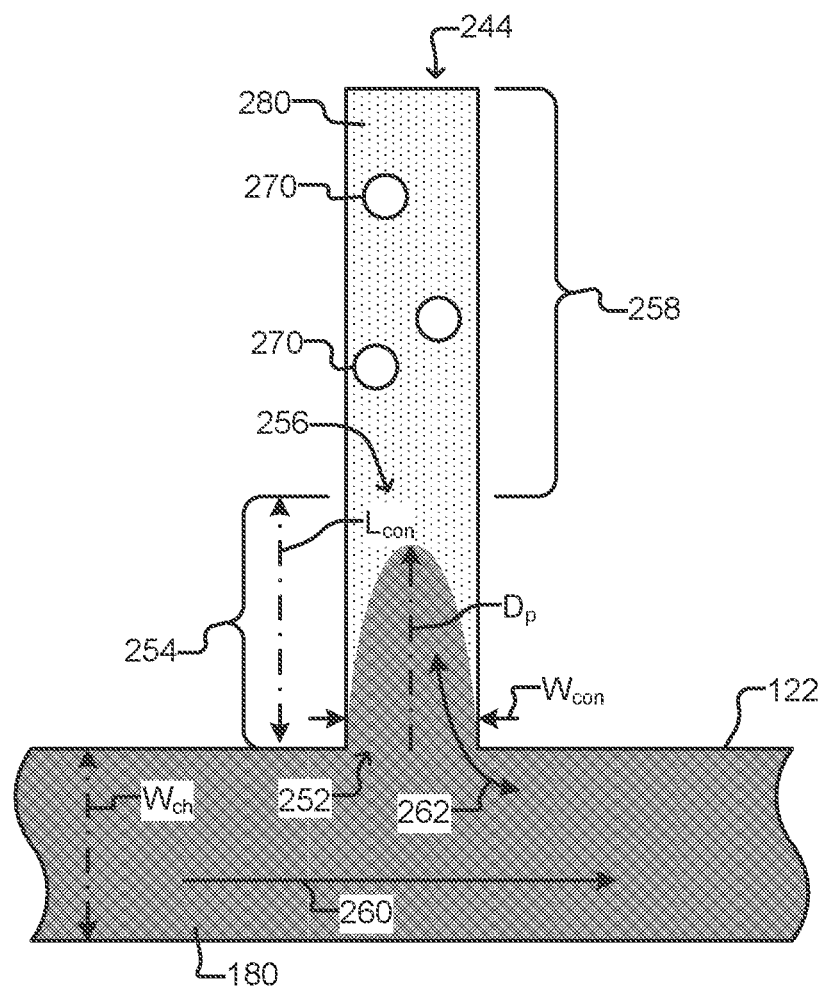
FIG. 2E provides a detailed illustration of a sequestration pen according to some embodiments of the invention.

FIG. 2E illustrates a detailed view of an example of a sequestration pen 244 according to the present invention. Examples of micro-objects 270 are also shown.

As is known, a flow 260 of fluidic medium 180 in a microfluidic channel 122 past a proximal opening 252 of sequestration pen 244 can cause a secondary flow 262 of the medium 180 into and/or out of the sequestration pen 244. To isolate micro-objects 270 in the isolation region 258 of a sequestration pen 244 from the secondary flow 262, the length $L_{con}$ of the connection region 254 of the sequestration pen 244 (i.e., from the proximal opening 252 to the distal opening 256) should be greater than the penetration depth $D_p$ of the secondary flow 262 into the connection region 254. The penetration depth $D_p$ of the secondary flow 262 depends upon the velocity of the fluidic medium 180 flowing in the channel 122 and various parameters relating to the configuration of the channel 122 and the proximal opening 252 of the connection region 254 to the channel 122. For a given microfluidic device, the configurations of the channel 122 and the opening 252 will be fixed, whereas the rate of flow 260 of fluidic medium 180 in the channel 122 will be variable. Accordingly, for each sequestration pen 244, a maximal velocity $V_{max}$ for the flow 260 of fluidic medium 180 in channel 122 can be identified that ensures that the penetration depth $D_p$ of the secondary flow 262 does not exceed the length $L_{con}$ of the connection region 254. As long as the rate of the flow 260 of fluidic medium 180 in the channel 122 does not exceed the maximum velocity $V_{max}$, the resulting secondary flow 262 can be limited to the channel 122 and the connection region 254 and kept out of the isolation region 258. The flow 260 of medium 180 in the channel 122 will thus not draw micro-objects 270 out of the isolation region 258. Rather, micro-objects 270 located in the isolation region 258 will stay in the isolation region 258 regardless of the flow 260 of fluidic medium 180 in the channel 122.

Moreover, as long as the rate of flow 260 of medium 180 in the channel 122 does not exceed $V_{max}$, the flow 260 of fluidic medium 180 in the channel 122 will not move miscellaneous particles (e.g., microparticles and/or nanoparticles) from the channel 122 into the isolation region 258 of a sequestration pen 244. Having the length $L_{con}$ of the connection region 254 be greater than the maximum penetration depth $D_p$ of the secondary flow 262 can thus prevent contamination of one sequestration pen 244 with miscellaneous particles from the channel 122 or another sequestration pen (e.g., sequestration pens 246, 248 in FIG. 2D).

Because the channel 122 and the connection regions 254 of the sequestration pens 244, 246, 248 can be affected by the flow 260 of medium 180 in the channel 122, the channel 122 and connection regions 254 can be deemed swept (or flow) regions of the microfluidic device 240. The isolation regions 258 of the sequestration pens 244, 246, 248, on the other hand, can be deemed unswept (or non-flow) regions. For example, components (not shown) in a first fluidic medium 180 in the channel 122 can mix with a second fluidic medium 280 in the isolation region 258 substantially only by diffusion of components of the first medium 180 from the channel 122 through the connection region 254 and into the second fluidic medium 280 in the isolation region 258. Similarly, components (not shown) of the second medium 280 in the isolation region 258 can mix with the first medium 180 in the channel 122 substantially only by diffusion of components of the second medium 280 from the isolation region 258 through the connection region 254 and into the first medium 180 in the channel 122. The first medium 180 can be the same medium or a different medium than the second medium 280. Moreover, the first medium 180 and the second medium 280 can start out being the same, then become different (e.g., through conditioning of the second medium 280 by one or more cells in the isolation region 258, or by changing the medium 180 flowing through the channel 122).

The maximum penetration depth $D_p$ of the secondary flow 262 caused by the flow 260 of fluidic medium 180 in the channel 122 can depend on a number of parameters, as mentioned above. Examples of such parameters include: the shape of the channel 122 (e.g., the channel can direct medium into the connection region 254, divert medium away from the connection region 254, or direct medium in a direction substantially perpendicular to the proximal opening 252 of the connection region 254 to the channel 122); a width $W_{ch}$ (or cross-sectional area) of the channel 122 at the proximal opening 252; and a width $W_{con}$ (or cross-sectional area) of the connection region 254 at the proximal opening 252; the velocity V of the flow 260 of fluidic medium 180 in the channel 122; the viscosity of the first medium 180 and/or the second medium 280, or the like.

In some embodiments, the dimensions of the channel 122 and sequestration pens 244, 246, 248 can be oriented as follows with respect to the vector of the flow 260 of fluidic medium 180 in the channel 122: the channel width $W_{ch}$ (or cross-sectional area of the channel 122) can be substantially perpendicular to the flow 260 of medium 180; the width $W_{con}$ (or cross-sectional area) of the connection region 254 at opening 252 can be substantially parallel to the flow 260 of medium 180 in the channel 122; and/or the length $L_{con}$ of the connection region can be substantially perpendicular to the flow 260 of medium 180 in the channel 122. The foregoing are examples only, and the relative position of the channel 122 and sequestration pens 244, 246, 248 can be in other orientations with respect to each other.

As illustrated in FIG. 2E, the width $W_{con}$ of the connection region 254 can be uniform from the proximal opening 252 to the distal opening 256. The width $W_{con}$ of the connection region 254 at the distal opening 256 can thus be in any of the ranges identified herein for the width $W_{con}$ of the connection region 254 at the proximal opening 252. Alternatively, the width $W_{con}$ of the connection region 254 at the distal opening 256 can be larger than the width $W_{con}$ of the connection region 254 at the proximal opening 252.

As illustrated in FIG. 2E, the width of the isolation region 258 at the distal opening 256 can be substantially the same as the width $W_{con}$ of the connection region 254 at the proximal opening 252. The width of the isolation region 258 at the distal opening 256 can thus be in any of the ranges identified herein for the width $W_{con}$ of the connection region 254 at the proximal opening 252. Alternatively, the width of the isolation region 258 at the distal opening 256 can be larger or smaller than the width $W_{con}$ of the connection region 254 at the proximal opening 252. Moreover, the distal opening 256 may be smaller than the proximal opening 252 and the width $W_{con}$ of the connection region 254 may be narrowed between the proximal opening 252 and distal opening 256. For example, the connection region 254 may be narrowed between the proximal opening and the distal opening, using a variety of different geometries (e.g. chamfering the connection region, beveling the connection region). Further, any part or subpart of the connection region 254 may be narrowed (e.g. a portion of the connection region adjacent to the proximal opening 252).

In various embodiments of sequestration pens (e.g. 124, 126, 128, 130, 244, 246 or 248), the isolation region (e.g. 258) is configured to contain a plurality of micro-objects. In other embodiments, the isolation region can be configured to contain only one, two, three, four, five, or a similar relatively small number of micro-objects. Accordingly, the volume of an isolation region can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more.

In various embodiments of sequestration pens, the width $W_{ch}$ of the channel 122 at a proximal opening (e.g. 252) can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the channel 122 can be in other ranges (e.g., a range defined by any of the endpoints listed above). Moreover, the $W_{ch}$ of the channel 122 can be selected to be in any of these ranges in regions of the channel other than at a proximal opening of a sequestration pen.

In some embodiments, a sequestration pen has a cross-sectional height of about 30 to about 200 microns, or about 50 to about 150 microns. In some embodiments, the sequestration pen has a cross-sectional area of about 100,000 to about 2,500,000 square microns, or about 200,000 to about 2,000,000 square microns. In some embodiments, a connection region has a cross-sectional height that matches the cross-sectional height of the corresponding sequestration pen. In some embodiments, the connection region has a cross-sectional width of about 50 to about 500 microns, or about 100 to about 300 microns.

In various embodiments of sequestration pens the height $H_{ch}$ of the channel 122 at a proximal opening 252 can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel 122 can be in other ranges (e.g., a range defined by any of the endpoints listed above). The height $H_{ch}$ of the channel 122 can be selected to be in any of these ranges in regions of the channel other than at a proximal opening of a sequestration pen.

In various embodiments of sequestration pens a cross-sectional area of the channel 122 at a proximal opening 252 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 122 at a proximal opening 252 can be in other ranges (e.g., a range defined by any of the endpoints listed above).

In various embodiments of sequestration pens, the length $L_{con}$ of the connection region 254 can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 254 can be in a different ranges than the foregoing examples (e.g., a range defined by any of the endpoints listed above).

In various embodiments of sequestration pens the width $W_{con}$ of a connection region 254 at a proximal opening 252 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 254 at a proximal opening 252 can be different than the foregoing examples (e.g., a range defined by any of the endpoints listed above).

In various embodiments of sequestration pens the width $W_{con}$ of a connection region 254 at a proximal opening 252 can be in any of the following ranges: 2-35 microns microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 254 at a proximal opening 252 can be different than the foregoing examples (e.g., a range defined by any of the endpoints listed above).

In various embodiments of sequestration pens, a ratio of the length $L_{con}$ of a connection region 254 to a width $W_{con}$ of the connection region 254 at the proximal opening 252 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 254 to a width $W_{con}$ of the connection region 254 at the proximal opening 252 can be different than the foregoing examples.

In various embodiments of microfluidic devices 100, 200, 240, 290, $V_{max}$ can be set around 0.2, 0.3, 0.4, 0.5, 0.6, 0.7, 0.8, 0.9, 1.0, 1.1, 1.2, 1.3, 1.4, or 1.5 μL/sec.

In various embodiments of microfluidic devices having sequestration pens, the volume of an isolation region 258 of a sequestration pen can be, for example, at least $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$ cubic microns, or more. In various embodiments of microfluidic devices having sequestration pens, the volume of a sequestration pen may be about $5\times10^3$, $7\times10^3$, $1\times10^4$, $3\times10^4$, $5\times10^4$, $8\times10^4$, $1\times10^5$, $2\times10^5$, $4\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some embodiments, the microfluidic device has sequestration pens wherein no more than $1\times10^2$ biological cells may be maintained, and the volume of a sequestration pen may be no more than $2\times10^6$ cubic microns. In some embodiments, the microfluidic device has sequestration pens wherein no more than $1\times10^2$ biological cells may be maintained, and a sequestration pen may be no more than $4\times10^5$ cubic microns. In yet other embodiments, the microfluidic device has sequestration pens wherein no more than 50 biological cells may be maintained, a sequestration pen may be no more than $4\times10^5$ cubic microns.

In various embodiment, the microfluidic device has sequestration pens configured as in any of the embodiments discussed herein where the microfluidic device has about 100 to about 500 sequestration pens; about 200 to about 1000 sequestration pens, about 500 to about 1500 sequestration pens, about 1000 to about 2000 sequestration pens, or about 1000 to about 3500 sequestration pens.

In some other embodiments, the microfluidic device has sequestration pens configured as in any of the embodiments discussed herein where the microfluidic device has about 1500 to about 3000 sequestration pens, about 2000 to about 3500 sequestration pens, about 2500 to about 4000 sequestration pens, about 3000 to about 4500 sequestration pens, about 3500 to about 5000 sequestration pens, about 4000 to about 5500 sequestration pens, about 4500 to about 6000 sequestration pens, about 5000 to about 6500 sequestration pens, about 5500 to about 7000 sequestration pens, about 6000 to about 7500 sequestration pens, about 6500 to about 8000 sequestration pens, about 7000 to about 8500 sequestration pens, about 7500 to about 9000 sequestration pens, about 8000 to about 9500 sequestration pens, about 8500 to about 10,000 sequestration pens, about 9000 to about 10,500 sequestration pens, about 9500 to about 11,000 sequestration pens, about 10,000 to about 11,500 sequestration pens, about 10,500 to about 12,000 sequestration pens, about 11,000 to about 12,500 sequestration pens, about 11,500 to about 13,000 sequestration pens, about 12,000 to about 13,500 sequestration pens, about 12,500 to about 14,000 sequestration pens, about 13,000 to about 14,500 sequestration pens, about 13,500 to about 15,000 sequestration pens, about 14,000 to about 15,500 sequestration pens, about 14,500 to about 16,000 sequestration pens, about 15,000 to about 16,500 sequestration pens, about 15,500 to about 17,000 sequestration pens, about 16,000 to about 17,500 sequestration pens, about 16,500 to about 18,000 sequestration pens, about 17,000 to about 18,500 sequestration pens, about 17,500 to about 19,000 sequestration pens, about 18,000 to about 19,500 sequestration pens, about 18,500 to about 20,000 sequestration pens, about 19,000 to about 20,500 sequestration pens, about 19,500 to about 21,000 sequestration pens, or about 20,000 to about 21,500 sequestration pens.

Figure 2F:
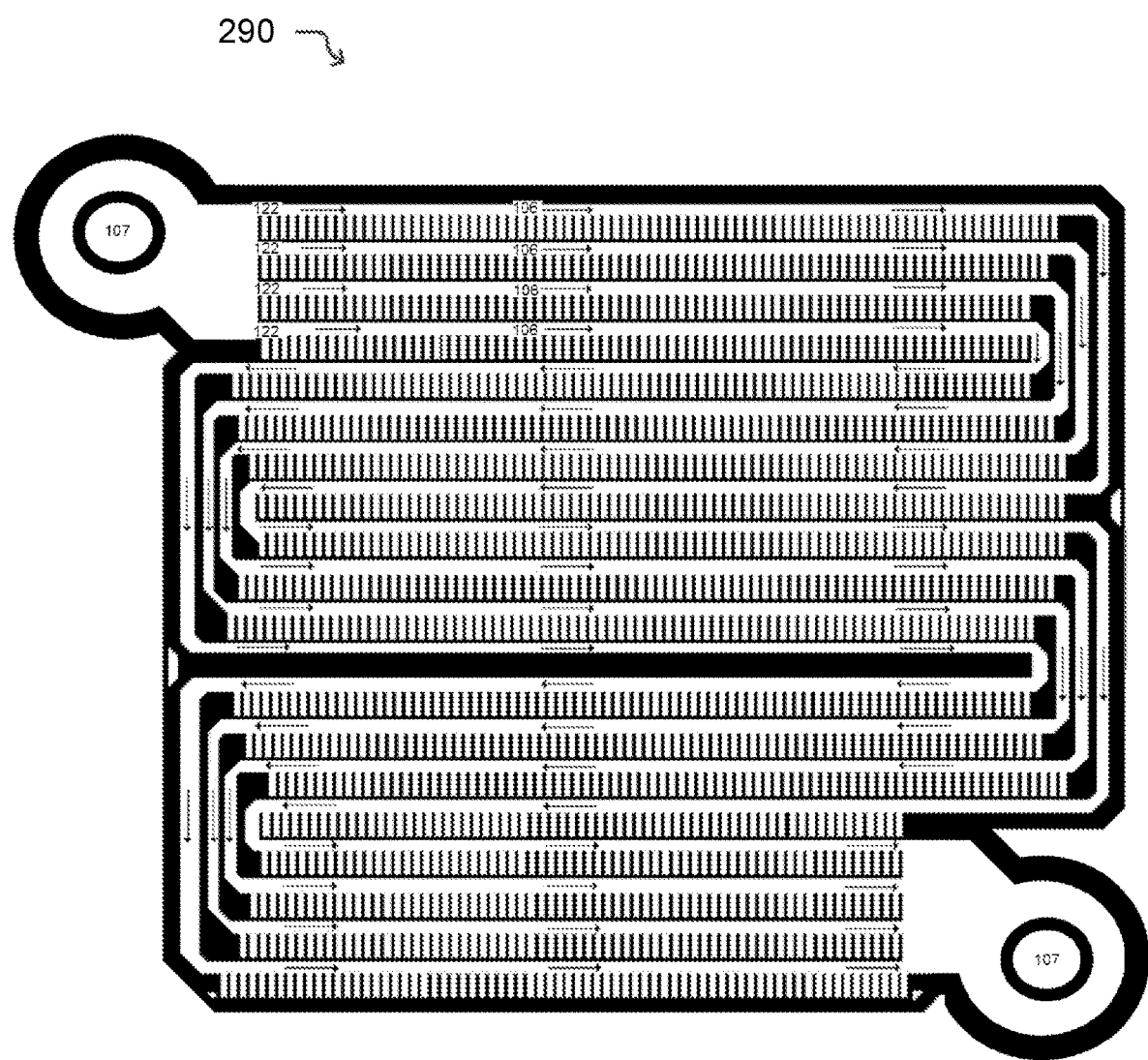
FIG. 2F illustrates a microfluidic device according to an embodiment of the invention.

FIG. 2F illustrates a microfluidic device 290 according to one embodiment. The microfluidic device 290 is illustrated in FIG. 2F is a stylized diagram of a microfluidic device 100. In practice the microfluidic device 290 and its constituent circuit elements (e.g. channels 122 and sequestration pens 128) would have the dimensions discussed herein. The microfluidic circuit 120 illustrated in FIG. 2F has two ports 107, four distinct channels 122 and four distinct flow paths 106. The microfluidic device 290 further comprises a plurality of sequestration pens opening off of each channel 122. In the microfluidic device illustrated in FIG. 2F, the sequestration pens have a geometry similar to the pens illustrated in FIG. 2E and thus, have both connection regions and isolation regions. Accordingly, the microfluidic circuit 120 includes both swept regions (e.g. channels 122 and portions of the connection regions 254 within the maximum penetration depth $D_p$ of the secondary flow 262) and non-swept regions (e.g. isolation regions 258 and portions of the connection regions 254 not within the maximum penetration depth $D_p$ of the secondary flow 262).

Figure 3A:
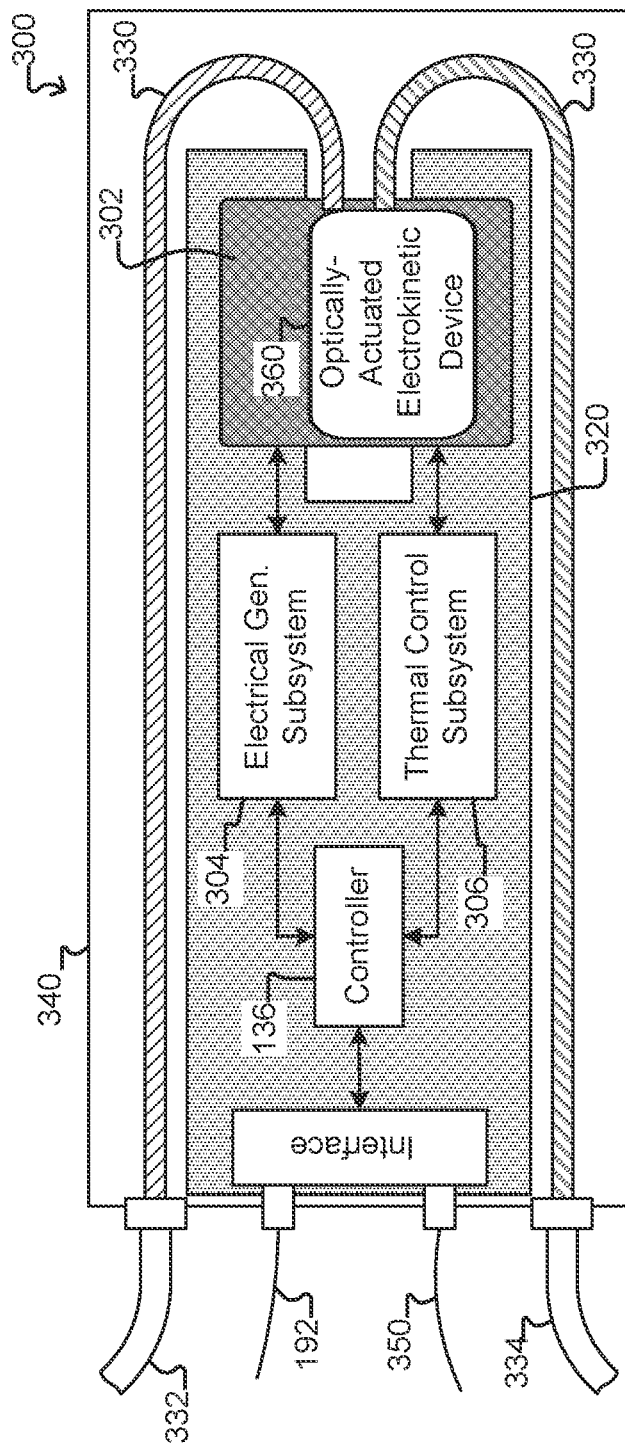
FIG. 3A illustrates a specific example of a system for use with a microfluidic device and associated control equipment according to some embodiments of the invention.
Figure 3B:
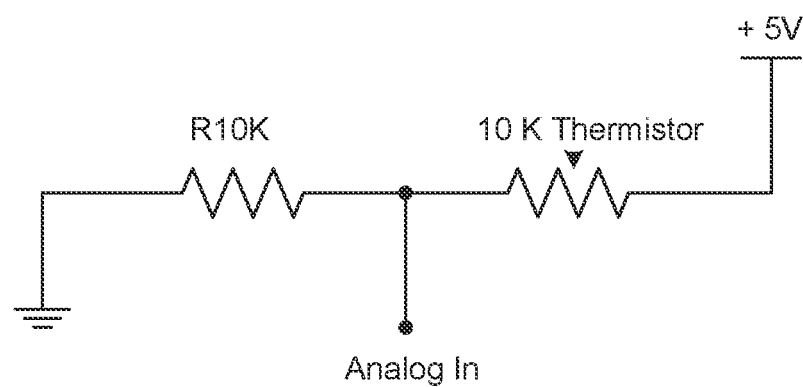
FIG. 3B illustrates an exemplary analog voltage divider circuit according to some embodiments of the invention.

FIGS. 3A through 3D shows various embodiments of system 150 which can be used to operate and observe microfluidic devices (e.g. 100, 200, 240, 290) according to the present invention. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 360 (e.g., an optically-actuated electrokinetic device 100) and providing electrical connections from power source 192 to microfluidic device 360. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 360 when it is being held by socket 302. Thus, the electrical signal generation subsystem 304 can be part of power source 192. The ability to apply a biasing voltage to microfluidic device 360 does not mean that a biasing voltage will be applied at all times when the microfluidic device 360 is held by the socket 302. Rather, in most cases, the biasing voltage will be applied intermittently, e.g., only as needed to facilitate the generation of electrokinetic forces, such as dielectrophoresis or electro-wetting, in the microfluidic device 360.

As illustrated in FIG. 3A, the nest 300 can include a printed circuit board assembly (PCBA) 320. The electrical signal generation subsystem 304 can be mounted on and electrically integrated into the PCBA 320. The exemplary support includes socket 302 mounted on PCBA 320, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 360 held by the socket 302. In certain embodiments, the oscilloscope measures the waveform at a location proximal to the microfluidic device 360 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya™ unit") and a waveform amplification circuit that amplifies the waveform generated by the Red Pitaya™ unit and passes the amplified voltage to the microfluidic device 100. In some embodiments, the Red Pitaya™ unit is configured to measure the amplified voltage at the microfluidic device 360 and then adjust its own output voltage as needed such that the measured voltage at the microfluidic device 360 is the desired value. In some embodiments, the waveform amplification circuit can have a +6.5V to −6.5V power supply generated by a pair of DC-DC converters mounted on the PCBA 320, resulting in a signal of up to 13 Vpp at the microfluidic device 360.

As illustrated in FIG. 3A, the nest 300 can further include a thermal control subsystem 306. The thermal control subsystem 306 can be configured to regulate the temperature of microfluidic device 360 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 360. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 330 configured to circulate cooled fluid through the cooling block. In the embodiment illustrated in FIG. 3A, the support structure 300 comprises an inlet 332 and an outlet 334 to receive cooled fluid from an external reservoir (not shown), introduce the cooled fluid into the fluidic path 330 and through the cooling block, and then return the cooled fluid to the external reservoir. In some embodiments, the Peltier thermoelectric device, the cooling unit, and/or the fluidic path 330 can be mounted on a casing 340 of the support structure 300. In some embodiments, the thermal control subsystem 306 is configured to regulate the temperature of the Peltier thermoelectric device so as to achieve a target temperature for the microfluidic device 360. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (shown in FIG. 3B) which includes a resistor (e.g., with resistance 1 kOhm+/−0.1%, temperature coefficient+/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

Figure 3C:
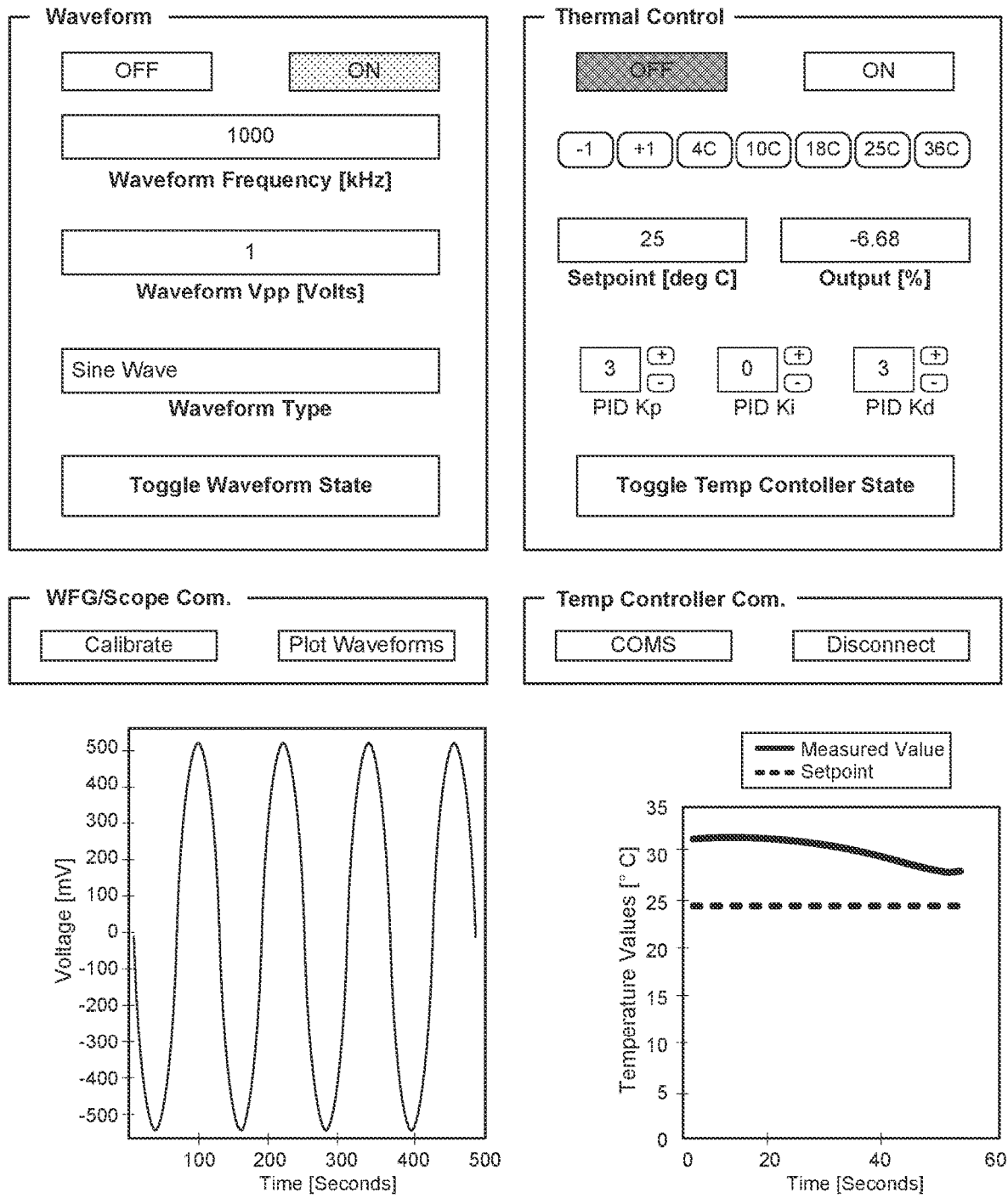
FIG. 3C illustrates an exemplary GUI configured to plot temperature and waveform data according to some embodiments of the invention.

The nest 300 can include a serial port 350 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 350, the electrical signal generation subsystem 308 and the thermal control subsystem 306 can communicate with the external master controller 154. In this manner, the master controller 154 can, among other things, assist the electrical signal generation subsystem 308 by performing scaling calculations for output voltage adjustments. A Graphical User Interface (GUI), one example of which is shown in FIG. 3C, provided via a display device 170 coupled to the external master controller 154, can be configured to plot temperature and waveform data obtained from the thermal control subsystem 306 and the electrical signal generation subsystem 308, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 404. The light modulating subsystem 404 can include a digital mirror device (DMD) or a microshutter array system (MSA), either of which can be configured to receive light from a light source 402 and transmits a subset of the received light into an optical train of microscope 400. Alternatively, the light modulating subsystem 404 can include a device that produces its own light (and thus dispenses with the need for a light source 402), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 404 can be, for example, a projector. Thus, the light modulating subsystem 404 can be capable of emitting both structured and unstructured light. One example of a suitable light modulating subsystem 404 is the Mosaic™ system from Andor Technologies™. In certain embodiments, imaging module 164 and/or motive module 162 of system 150 can control the light modulating subsystem 404.

In certain embodiments, the imaging device 194 further comprises a microscope 400. In such embodiments, the nest 300 and light modulating subsystem 404 can be individually configured to be mounted on the microscope 400. The microscope 400 can be, for example, a standard research-grade light microscope or fluorescence microscope. Thus, the nest 300 can be configured to be mounted on the stage 410 of the microscope 400 and/or the light modulating subsystem 404 can be configured to mount on a port of microscope 400. In other embodiments, the nest 300 and the light modulating subsystem 404 described herein can be integral components of microscope 400.

In certain embodiments, the microscope 400 can further include one or more detectors 422. In some embodiments, the detector 422 is controlled by the imaging module 164. The detector 422 can include an eye piece, a charge-coupled device (CCD), a camera (e.g., a digital camera), or any combination thereof. If at least two detectors 422 are present, one detector can be, for example, a fast-frame-rate camera while the other detector can be a high sensitivity camera. Furthermore, the microscope 400 can include an optical train configured to receive reflected and/or emitted light from the microfluidic device 360 and focus at least a portion of the reflected and/or emitted light on the one or more detectors 422. The optical train of the microscope can also include different tube lenses (not shown) for the different detectors, such that the final magnification on each detector can be different.

In certain embodiments, imaging device 194 is configured to use at least two light sources. For example, a first light source 402 can be used to produce structured light (e.g., via the light modulating subsystem 404) and a second light source 432 can be used to provide unstructured light. The first light source 402 can produce structured light for optically-actuated electrokinesis and/or fluorescent excitation, and the second light source 432 can be used to provide bright field illumination. In these embodiments, the motive module 162 can be used to control the first light source 404 and the imaging module 164 can be used to control the second light source 432. The optical train of the microscope 400 can be configured to (1) receive structured light from the light modulating subsystem 404 and focus the structured light on at least a first region in a microfluidic device, such as an optically-actuated electrokinetic device, when the device is being held by the support structure 200, and (2) receive reflected and/or emitted light from the microfluidic device and focus at least a portion of such reflected and/or emitted light onto detector 422. The optical train can be further configured to receive unstructured light from a second light source and focus the unstructured light on at least a second region of the microfluidic device, when the device is held by the support structure 300. In certain embodiments, the first and second regions of the microfluidic device can be overlapping regions. For example, the first region can be a subset of the second region.

Figure 3D:
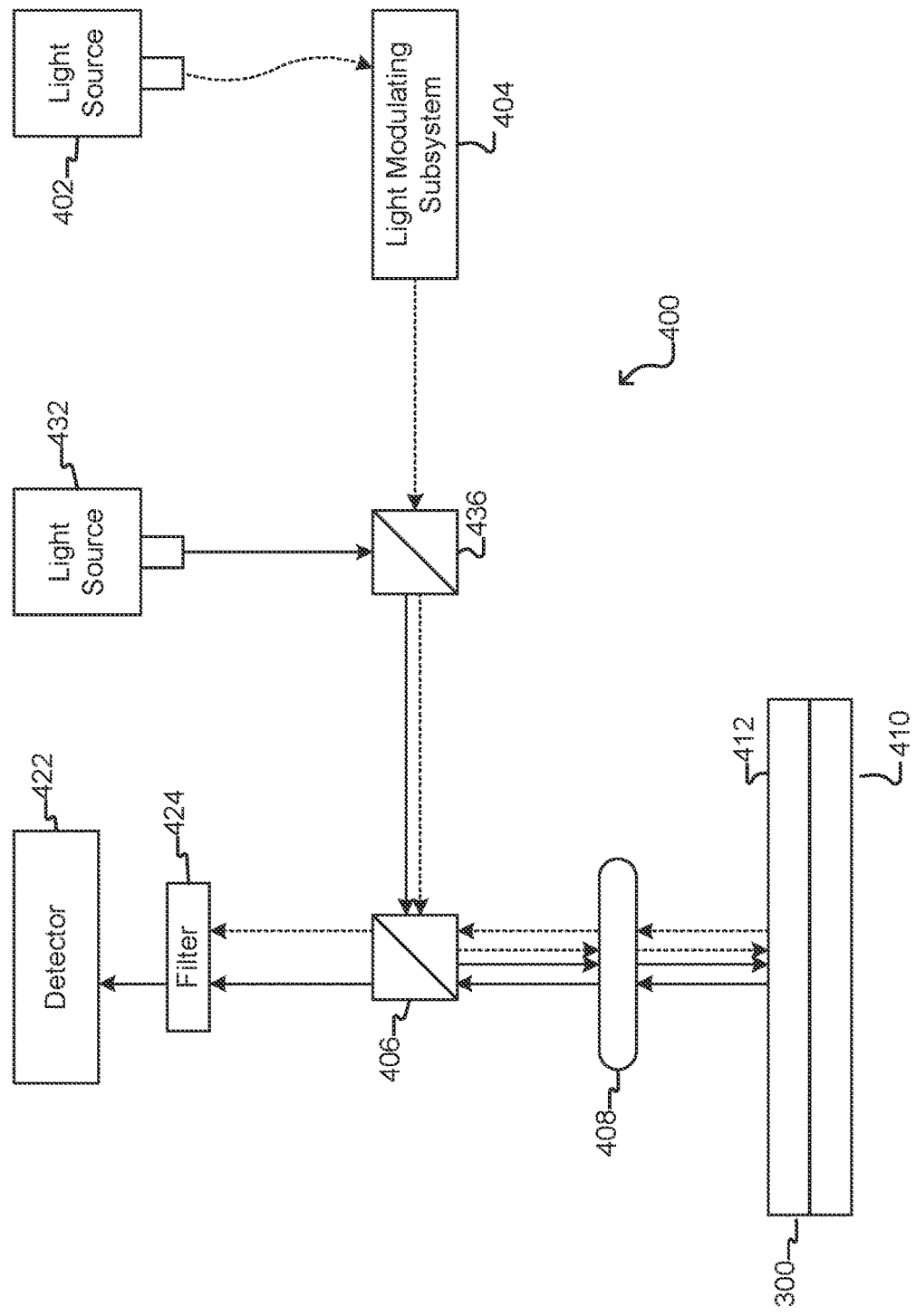
FIG. 3D illustrates an imaging device according to some embodiments of the invention.

In FIG. 3D, the first light source 402 is shown supplying light to a light modulating subsystem 404, which provides structured light to the optical train of the microscope 400. The second light source 432 is shown providing unstructured light to the optical train via a beam splitter 436. Structured light from the light modulating subsystem 404 and unstructured light from the second light source 432 travel from the beam splitter 436 through the optical train together to reach a second beam splitter (or dichroic filter 406, depending on the light provided by the light modulating subsystem 404) where the light gets reflected down through the objective 408 to the sample plane 412. Reflected and/or emitted light from the sample plane 412 then travels back up through the objective 408, through the beam splitter and/or dichroic filter 406, and to another dichroic filter 424. Only a fraction of the light reaching dichroic filter 424 passes through and reaches the detector 422.

In some embodiments, the second light source 432 emits blue light. With an appropriate dichroic filter 424, blue light reflected from the sample plane 412 is able to pass through dichroic filter 424 and reach the detector 422. In contrast, structured light coming from the light modulating subsystem 404 gets reflected from the sample plane 412, but does not pass through the dichroic filter 424. In this example, the dichroic filter 424 is filtering out visible light having a wavelength longer than 495 nm. Such filtering out of the light from the light modulating subsystem 404 would only be complete (as shown) if the light emitted from the light modulating subsystem did not include any wavelengths shorter than 495 nm. In practice, if the light coming from the light modulating subsystem 404 includes wavelengths shorter than 495 nm (e.g., blue wavelengths), then some of the light from the light modulating subsystem would pass through filter 424 to reach the detector 422. In such an embodiment, the filter 424 acts to change the balance between the amount of light that reaches the detector 422 from the first light source 402 and the second light source 432. This can be beneficial if the first light source 402 is significantly stronger than the second light source 432. In other embodiments, the second light source 432 can emit red light, and the dichroic filter 424 can filter out visible light other than red light (e.g., visible light having a wavelength shorter than 650 nm).

In some embodiments, the invention provides methods for the automated detection of assay-positive assay areas in a microfluidic device. The methods can include collecting a set of n digital images $I_i$ (i=1 to n) of an assay area $AA_x$ in a microfluidic device, where n is a positive integer greater than 1. In some embodiments, the methods include the automated identification (e.g., selection) of assay areas in a microfluidic device. Typically, methods performed for the automated detection of assay-positive areas will be performed by the imaging module 164 based on data received from the imaging device 194 (not shown), the media module 160, the motive module 162, the tilting module 166, other modules 168, and/or the master controller 154. However, as is appreciated by those skilled in the art, any of the steps involved in the automated-identification of assay-positive areas can be performed by any module or sub-module.

Because the assay is performed in a microfluidic device, the configuration (e.g. shape and dimensions) of the microfluidic circuit and its constituent circuit elements determines where the reagents and analytes that are used in the assay can be located within the microfluidic circuit. For example, assays may be performed to quantify proteins produced by single cells, or clonal populations of cells, located in sequestration pens. Similarly, reagents used in various assays (e.g. fluorophores or antibodies) can be introduced by flowing media containing the reagents through channels of the microfluidic circuit. As discussed above with respect to FIG. 2E, the shape and dimensions of a sequestration pen and a channel (individually and relative to each other) can influence where the proteins and reagents are physically located within the microfluidic circuit, and therefore the region of the device to be assayed.

Accordingly, the size and shape of the assay areas can be automatically identified based on a number of parameters including any combination of: the type of assay involved, the shape and dimensions of chambers (e.g., sequestration pens) and/or flow regions (e.g., channels) in the microfluidic circuit, the velocity of fluidic medium in the flow path, the viscosity of the fluidic medium and/or the presence of polymerization agents within the fluidic medium, the physical and chemical properties of the analytes measured in the assay (e.g. antibodies or secreted proteins), the physical and chemical properties of reagents used in the assay, the physical location of the reagents or analytes used in the assay, the number of cells being assayed (i.e. a single cell or a clonal population of cells), and/or the amount of noise and background produced by the analytes and/or reagents used in the assay. These methods are described in detail below with respect to FIGS. 4, 5 and 6.

Figure 4A:
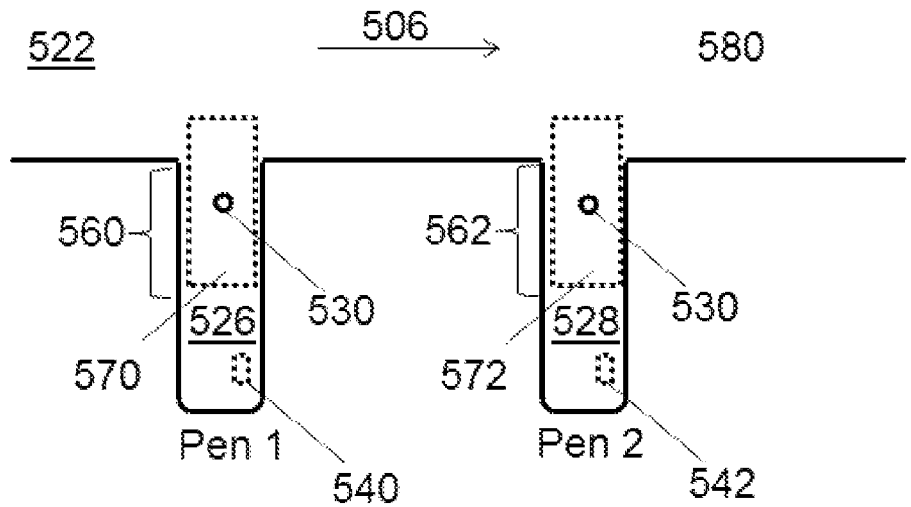
FIGS. 4A-4C illustrate automatically-identified assay areas according to some embodiments of the invention.

FIG. 4A shows exemplary automatically-identified assay areas having rectangular shapes 570, 572 that are located partially in the flow channel 522 and located partially in sequestration pens 526, 528. For assays involving an analyte and/or reagent that is contained within the fluidic medium 580 in a flow path 506 within the channel 522, the imaging module 164 (not shown) is configured to automatically identify (or select) an assay area 570, 572 that extends, at least partially, into a region of the channel 522 proximal to the opening of a sequestration pen. The assay area 570, 572 may also be identified based on the position of a micro-object 530 (e.g. a cell) within the sequestration pen. For example, as shown, the assay areas 570, 572 can be selected such that they encompass the location of the micro-object 530 in the sequestration pen 526, 528. Computational methods of determining the position of a micro-object by automatically identifying micro-objects are discussed in U.S. application Ser. No. 14/963,230 (Du) and corresponding International Application No. PCT/US2015/064575, each filed on Dec. 8, 2015; the entire contents of each application are herein incorporated by reference. In addition to these methods, the position of a micro-object in a pen can also be estimated based on other information such as the method by which the micro-objects were loaded into the pen (e.g. by gravity or OET) and in instances where the micro-objects are cells, the duration of time that the cells were cultured in the pen and/or the cell type. Thus, depending on other parameters as discussed above, the automatically-identified assay area 570, 572 can be located at least partially in a region of a sequestration pen 526, 528 proximal to the channel 522 (e.g., the proximal opening of the sequestration pen and/or the connection region, or a proximal portion thereof, of the sequestration pen). In some instances, the depth of the automatically-identified assay areas 570, 572 in the sequestration pens 526, 528 will be based in part, on the maximum penetration depth $D_p$ of the secondary flow (not shown) into the connection region 560, 562 of the sequestration pen 526, 528. As discussed above, the maximum penetration depth $D_p$ of the secondary flow can be based on many factors, including the dimensions (e.g. the width) of the proximal opening of the sequestration pen 526, 528 and channel 522, the viscosity of the fluidic medium, and the velocity of the fluidic medium as it moves along the flow path 506. FIG. 4A also illustrates exemplary control regions $L_{ctrl}$ 540, 542 associated with the automatically-identified assay areas 570, 572. The use of control regions to quantify a rate of change for an assay area is discussed in detail below.

Figure 4B:
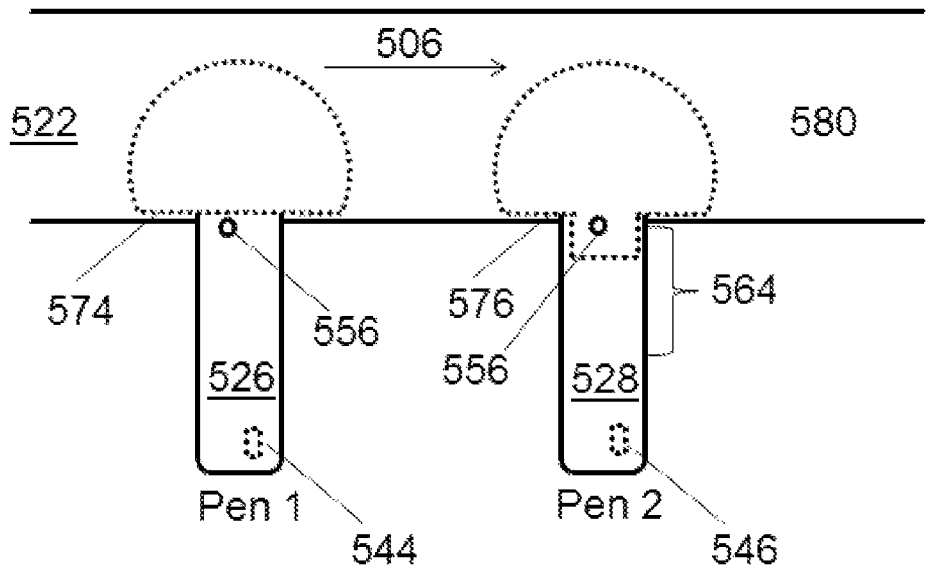

For certain assays, such as assays designed to quantify the amount of an analyte that is secreted ("secreted analyte") from biological micro-object(s) within a sequestration pen 528, the imaging module 164 is configured to automatically identify an assay area based, at least in part, on an area of diffusion of the secreted analyte into the area of the channel 522 surrounding the biological micro-object 556 and the sequestration pens 526, 528. FIG. 4B shows an exemplary automatically-identified assay area 574 having a truncated circular shape located entirely within the channel 522, adjacent to a sequestration pen 526 containing a biological micro-object 556. In addition, FIG. 4B shows an automatically-identified assay area 576 having a mushroom-like shape that includes the truncated circular shape of assay area 574 and further extends partially into the connection region of a sequestration pen 528 containing a biological micro-object 556. The extent to which the semi-circle shape or the mushroom-like shape of assay areas 574, 576 extend into the channel 522 can be based on a number of factors, such as the rate of diffusion of the secreted analyte, the viscosity of the fluidic medium 580, the dimensions of the channel 522 and/or the sequestration pen 526, 528, and/or the physical location of the biological micro-objects 556 secreting the analyte.

Figure 4C:
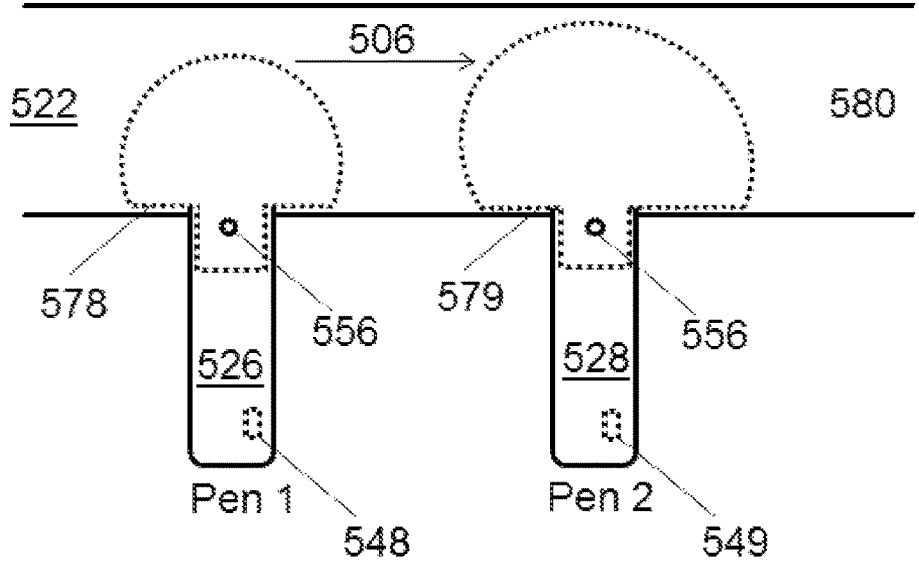

In some instances, the size of the automatically-identified assay area can depend on the duration of time over which the area is assayed. For example, in instances where the automatically-identified assay area is analyzed over a long duration of time (i.e. several images of the assay area are taken over a significant duration of time), the automatically-identified assay area can be augmented (e.g. enlarged) to account for a rate of diffusion of a reagent or an analyte. FIG. 4C shows two mushroom-like assay areas 578, 579 corresponding to a first time point ($T_1$) and a second time point ($T_2$), respectively. The mushroom-like assay area 579 corresponding to the second time point ($T_2$) extends into a greater portion of the channel 522 than the mushroom-like assay area 578 corresponding to the first time point ($T_1$) to account for the rate of diffusion of a reagent or analyte in the time period between the first time point and the second time point.

In some embodiments, assays may involve an analyte or reagent that is affixed (e.g. by adhering the analyte or reagent, or limiting the motion and/or diffusion of the analyte or reagent) to a specific area and/or feature of the microfluidic circuit ("affixed analyte or reagent"), such as a sequestration pen, a trap, or a portion of a channel. In these instances, the imaging module may automatically identify an assay area based on data specifying the location of the affixed analyte. In some instances, the analyte or reagent may be affixed to a specific portion of the microfluidic device (e.g. a portion of a channel or a sequestration pen) using a polymer network. For example, structured light may be used to generate a localized network of polymers containing a reagent or analyte through a light-induced polymerization/cross-linking reaction that solidifies the polymers by cross linking the polymers into a network. The localized polymer network can slow the rate of diffusion of the reagent and/or the analyte, and thereby maintain the reagent and analyte in close proximity within the polymer network, in order to optimize the assay (e.g., by concentrating the assay signal). In these embodiments, the imaging module 164 communicates with the motive module 162 to transmit information specifying the portion of the microfluidic device where the polymerization/cross-linking has occurred. The imaging module 164 then uses this area to automatically identify an assay area corresponding, at least in part, to the location of the resulting polymer network.

Regardless of the size and shape of the automatically-identified assay area, the automatically-identified assay area will generally be limited to a region that is entirely within the chamber of the microfluidic device (i.e., it will not include walls, or portions of the microfluidic circuit material, that define the flow channel and/or the sequestration pens).

In certain embodiments, the set of n digital images $I_i$ (i=1 to n) of an automatically-identified assay area $AA_x$ are collected using a digital camera or a CCD. However, collected images that are initially non-digitized can be digitized following collection. The images are typically collected in a periodic manner, with the period being dependent upon the assay. In certain embodiments, images of a particular automatically-identified assay area can be taken every minute, every 2 minutes, every 3 minutes, every 4 minutes, every 5 minutes, etc., depending on the rate and density of secretion and/or the rate at which the assay signal develops. In certain embodiments, the assay is an antigen binding assay, and the period for taking images is once every 3 to 5 minutes.

The size of the digital images will vary according to the imaging device 194 used to collect the images. As discussed above, the size of the digital images may also vary with the size of the automatically-identified assay area $AA_x$ over the duration of the assay. In some embodiments, the image Idi of the assay area $AA_x$ includes at least about 500 pixels (e.g., about 500 to about 10,000 pixels, about 625 to about 8000 pixels, about 750 to about 6000 pixels, about 875 to about 4000 pixels, about 1000 to about 2000 pixels, or any similar range of pixels). For example, in some embodiments, an image $I_i$ can cover an assay area $AA_x$ with a rectangular array of pixels that is substantially 25 pixels by substantially 40 to 80 pixels. In some embodiments, each pixel can corresponds to an area in the microfluidic device of substantially 5 microns$^2$ or less (e.g., 4, 3, 2, 1 microns$^2$, or less).

After a digital image is collected, it is analyzed. In this regard, parameters that characterize the distribution of light intensity values for a set of pixels that make up the image $I_i$ of an automatically-identified assay area $AA_x$ can be determined. For example, the light intensity value $L_{i,j}$ of each pixel $P_{i,j}$ (j=1 to m) can be evaluated and/or recorded, where j is the number of pixels in the image $I_i$ (or an automatically-identified assay area $AA_x$ thereof) being analyzed. However, in some instances, only a subset of the set of pixels $P_{i,j}$ (j=1 to m) of the image Ii of the automatically-identified assay area $AA_x$ can be analyzed to determine the distribution of light intensity values that make up the image $I_i$. For example, less than 70%, 75%, 80%, 85%, 90%, 95%, 96%, 97%, 98%, 99%, 99.5% of the set of pixels $P_i$ (j=1 to m) of the image Ii of the automatically-identified assay area $AA_x$ may be analyzed to determine the distribution of light intensity values that make up the image $I_i$.

In certain embodiments, the light intensity values $L_{i,j}$ of each pixel $P_{i,j}$ is represented using 0-8 bits, 0-10 bits, 0-12 bits, 0-14 bits, or 0-16 bits. Using larger numbers of bits to represent the light intensity values $L_{i,j}$ can provide for superior analysis of weak signals.

In certain embodiments, determining the light intensity values $L_{i,j}$ can involve subtracting a background level of light intensity from the actual observed level of light intensity. For example, $L_{i,j}$ can be set equal to $L_{i,j}$(observed)−$L_{i,j}$(background). $L_{i,j}$(background) can be the light intensity value associated with the same pixel $P_j$ at the beginning of the assay (t=0) or just prior to the beginning of the assay (t<0) or during calibration of the apparatus (t=−T). Alternatively, $L_{i,j}$(background) can be $L_{con}$, the light intensity value of a control region of the microfluidic device (i.e., a region of the microfluidic device in which the assay is not expected to produce a positive signal). The control region $L_{con}$ can be, for example, a region in a sequestration pen that does not have any micro-objects therein. Thus, for example, the control region $L_{con}$ can be the same for two or more selected assay areas. Alternatively, each selected assay area can be associated with its own control region $L_{con}$. For example, the control region $L_{con}$ can be a region in the sequestration pen 526, 528 that is distal to the channel 522 and/or isolated from any fluid medium 180 in the channel 522 (e.g., such that the maximum penetration depth $D_p$ of secondary flow from the channel 522 does not extend into the control region $L_{con}$) such as any of control regions $L_{con}$ 540, 542, 544, 546, 548, 549.

Figure 5:
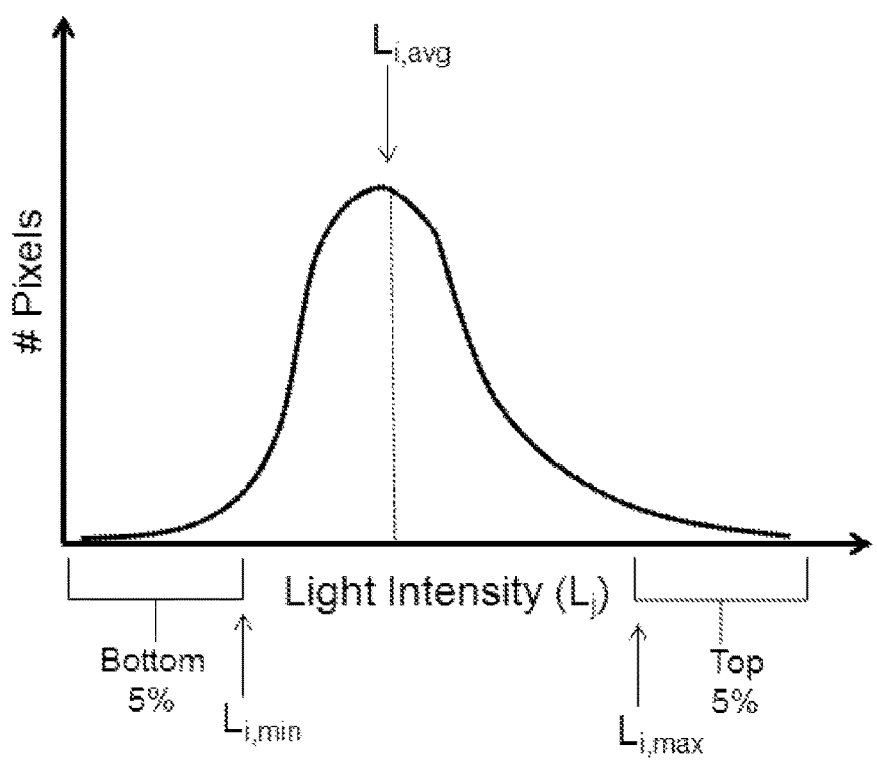
FIG. 5 is a graphical illustration of the distribution of pixels $P_{i,j}$ in an image as a function of their light intensity value $L_{i,j}$. The graph includes labels for the average light intensity value of the pixels $L_{i,avg}$, as well as the minimum and maximum light intensity values $L_{i,min}$ & $L_{i,max}$, after discarding pixels having a light intensity value in the bottom 5% and top 5%, respectively.

Using the set of light intensity values $L_{i,j}$ for the set of pixels $P_{i,j}$ (j=1 to m) from an image $I_i$, various statistical parameters can be determined. For example, the average light intensity value ($L_{i,avg}$), the standard deviation ($\sigma_i$) of the light intensity value, the minimum and maximum light intensity values ($L_{i,min}$ and $L_{i,max}$), or any combination thereof can be determined for the set of pixels $P_{i,j}$ (j=1 to m), and thus the image $I_i$ (or an automatically-identified assay area $AA_x$ thereof). Accordingly, in certain embodiments, the methods of the invention involve calculating $L_{i,avg}$, calculating $\sigma_i$, determining $L_{i,min}$, and/or determining $L_{i,max}$ for the set of pixels $P_{i,j}$ (j=1 to m) that make up image $I_i$ (or an automatically-identified assay area $AA_x$ thereof). For determination of $L_{i,min}$ and $L_{i,max}$, the values can correspond to the light intensity values $L_{i,j}$ for the pixels $P_{i,j}$ (j=1 to m) having the lowest and highest light intensity values, respectively. Alternatively, $L_{i,min}$ and $L_{i,max}$ can be determined after discarding a fixed percentage of pixels $P_{i,j}$ (j=1 to m) having the highest and lowest light intensity values. For example, as shown in FIG. 5, the light intensity values $L_{i,j}$ for the pixels $P_{i,j}$ in the bottom 5% of the distribution can be discarded and $L_{i,min}$ can be set as the lowest light intensity level of the remaining 95% of the pixels. Similarly, the light intensity values $L_{i,j}$ for the pixels $P_{i,j}$ in the top 5% of the distribution can be discarded and $L_{i,max}$ can be set as the highest light intensity level of the remaining 95% of the pixels. Of course, the percentage of discarded light intensity values can be set at a number other than 5%. For example, 10%, 9%, 8%, 7%, 6%, 4%, 3%, 2.5%, 2%, 1.5%, or 1% can be used in place of 5%. The optimal percentage can be determined empirically, through routine experimentation.

For each image $I_i$ in a set of n images L (i=1 to n) of an automatically-identified assay area, parameters that characterize the distribution of light intensity values for the set of pixels $P_{i,j}$ that make up the image $I_i$ of an automatically-identified assay area $AA_x$ can be determined, as discussed above. In certain embodiments, the parameters determined from each of the images in a set can be compared to one another. Thus, the methods of the invention can further include calculating a rate of change $\Delta_x$ of at least one parameter of a selected assay area $AA_x$ over the course of all or part of the assay (i.e., between two or more different images $I_i$ in the set of n images $I_i$ (i=1 to n)). In certain embodiments, the at least one parameter is selected from the group consisting of $L_{i,avg}$, $\sigma_i$, $L_{i,min}$, and $L_{i,max}$. In certain embodiments, $\Delta_x$ is a vector or other mathematical expression that represents the rate of change of two or more such parameters.

In certain embodiments, the methods of the invention further include comparing the rate of change $\Delta_x$ of the at least one parameter to a threshold value, $\Delta^\circ$, and determining that an automatically-identified assay region is assay-positive if $\Delta_x$ is greater than $\Delta^\circ$.

The methods of the invention can be applied to a plurality of k automatically-identified assay areas $AA_x$ (x=1 to k), where k is an integer greater than 1. The methods can be performed in parallel on the plurality of k automatically-identified assay areas. Alternatively, the methods can be performed serially on the plurality of k automatically-identified assay areas. In still other alternatives, certain steps of the methods can be performed on the plurality of k defined assay areas in parallel while other steps can be performed serially. Regardless, for a set of k automatically-identified assay areas, $\Delta_x$ can be determined for each automatically-identified assay area $AA_x$. In some embodiments, the size, shape, and relative position (i.e., with respect to a sequestration pen) of the automatically-identified assay areas $AA_x$ (x=1 to k) can be kept constant. In other embodiments, the size, shape, and relative position of an automatically-identified assay areas $AA_x$ (x=1 to k) can differ based on different parameters. For example, the size, shape and relative position of an automatically-identified assay area may vary according to factors such as the position of a cell or different known concentrations of an analyte used to create a calibration curve to determine a quantity of analyte under experimental conditions.

In certain embodiments, the methods of the invention include determining a rate of change for a set of automatically-identified assay areas $AA_x$. The methods of the invention can be applied to a plurality of k automatically-identified assay areas $AA_x$ (x=1 to k), where k is an integer greater than 1. Thus, in certain embodiments of the methods, an average rate of change $\Delta_{avg}$ for the rates of change $\Delta_x$ corresponding to the set of k automatically-identified assay areas $AA_x$ (x=1 to k) can be determined. In certain embodiments, a standard deviation $\sigma^\circ$ for the rates of change $\Delta_x$ of the set of k automatically-identified assay areas $AA_x$ (x=1 to k) can be determined. In certain embodiments, a calibration curve may be generated using the set of values $\Delta_x$ corresponding to the set of k automatically-identified assay areas $AA_x$ (x=1 to k), where each value $\Delta_x$ is associated with a known concentration of the analyte that is to be assayed.

In certain embodiments, the threshold $\Delta^\circ$ (discussed above) can be based on the average rate of change $\Delta_{avg}$ for the set of rates of change $\Delta_x$ corresponding to the set of k automatically-identified assay areas $AA_x$ (x=1 to k). In other embodiments, the threshold $\Delta^\circ$ (discussed above) can be based on the average rate of change $\Delta_{avg}$ and the standard deviation $\sigma^\circ$ for the set of rates of change $\Delta_x$ corresponding to the set of k automatically-identified assay areas $AA_x$ (x=1 to k). For example, the threshold $\Delta^\circ$ can be $\Delta_{avg}+1.6\sigma^\circ$. Alternatively, the threshold $\Delta^\circ$ can be $\Delta_{avg}+2.0\sigma^\circ$, $\Delta_{avg}+3.0\sigma^\circ$, $\Delta_{avg}+4.0\sigma^\circ$, or the like. In embodiments which use a calibration curve, an average rate of change $\Delta_x$ may be calculated for each set of automatically-identified assay areas $AA_x$ having the same known concentration of the analyte that is to be assayed. All of the above methods of image analysis may be performed iteratively on a set of images to determine an optimal assay area from the set of automatically-identified assay areas.

Figure 6:
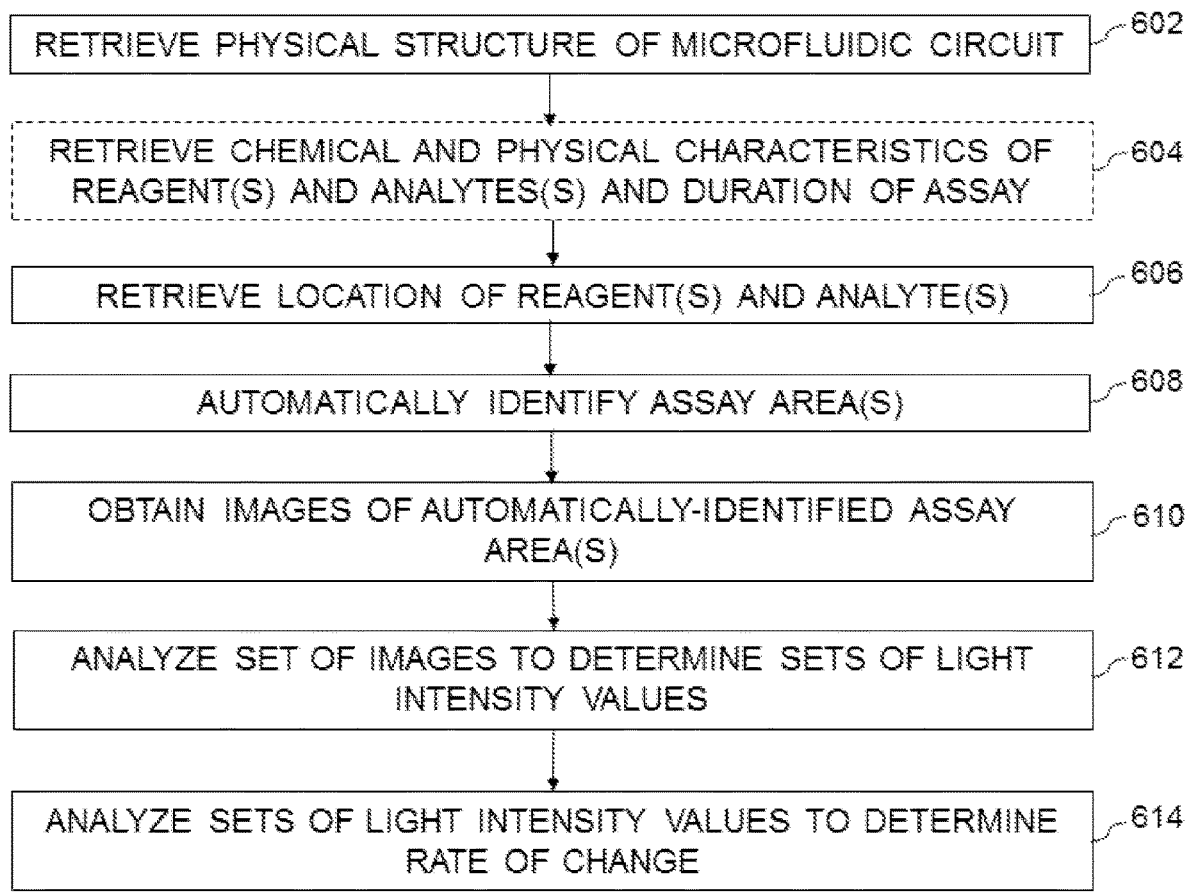
FIG. 6 illustrates a series of steps involved in determining a rate of change for an automatically-identified assay area according to one embodiment of the invention.

FIG. 6 illustrates steps that can be performed by the imaging module 164 to determine a rate of change $\Delta_x$ corresponding to an assay area $AA_x$. As is appreciated by those skilled in the art, several of the steps discussed below can be performed in any order and by modules or programs other than the imaging module 164. Similarly, the steps discussed blow may be performed iteratively.

At step 602, the imaging module 164 can retrieve information specifying the physical structure of the microfluidic circuit 120, including the dimensions of any sequestration pens 128, channels 122 or other physical features of the microfluidic circuit 120. Information may be calculated "on the fly" by the imaging module 164 based on images of the microfluidic circuit 120 or may be pre-specified (e.g. based on known dimensions and physical features of a certain type of microfluidic circuit 120) and stored in memory. The dimensions of the circuit elements may be used to model the flow of fluidic medium such as medium containing reagents and analytes used in the assay. The flow may be modeled using various programs and computational models (e.g. MATLAB® or COMSOL® software).

At step 604, the imaging module 164 optionally retrieves data specifying the physical and chemical characteristics of the analytes (e.g. antibodies, secreted proteins) and reagents (e.g. antigens, fluorophores, light-induced polymers, etc.) that are used in the assay, and/or any fluidic medium 180 in which the assay takes place. Physical and chemical characteristics may include molecular weight, hydrophobicity, solubility, rate of diffusion, viscosity (e.g., of the medium), excitation and/or emission range (e.g., of fluorescent reagents), known background fluorescence, characteristics influencing polymerization, and pore size of a localized polymer network. Data describing the physical and chemical characteristics of the analyte(s), reagents, and fluidic medium 180 may be input by a user of the microfluidic apparatus 100 or may be pre-computed and stored in memory. Optionally at step 604, the imaging module 164 can retrieve information specifying the duration of the assay.

At step 606, the imaging module 164 can retrieve information specifying the location (or projected location) of the reagent(s) and analyte(s) to be assayed within the microfluidic structure. As discussed above, the location of the reagent(s) and analyte(s) may be computed based on the dimensions of the microfluidic circuit and/or the type of assay being performed (e.g. secretion assay, antigen detection assay, etc.). In addition, programs and computational models used to model the flow of media (and reagent(s) present in a medium) in a microfluidic circuit can be used to determine a projected location of the reagent(s) and analyte(s). For example, the projected location of the reagent(s) and analyte(s) may be based on the maximum penetration depth $D_p$ of a secondary flow of medium flowing in the microfluidic circuit (e.g., in a flow region or channel) and any of the parameters that affect $D_p$ (e.g. velocity of the medium in the flow path, width of the flow path, width of the opening to a sequestration pen, etc.). Similarly, in instances where a biological micro-object such as a cell secretes an analyte, the location of the analyte may be based on the position of the biological micro-object in a circuit element (e.g. a sequestration pen). Any of the above values may be combined with the physical and chemical characteristics of the analyte(s) or reagents to further refine the location (or projected location) of the reagent(s) and/or analyte(s). For example, the location of an analyte that is secreted from a cell in a sequestration pen may be based on both a known diffusion rate of the analyte, the dimensions of the sequestration pen, and the viscosity of the medium.

As also described above, in instances where the motive module 162 is used to provide structured light to actuate polymerization/cross-linking of light-actuated polymers and form a light-actuated polymer network, the imaging module 164 may receive information from the motive module 162 specifying the location of the network of polymers containing the analyte and/or reagent(s) in the microfluidic circuit 120. In other instances, users of the system 150 may input the locations of the reagent(s) and/or analyte(s). In other instances, the locations of the reagent(s) and/or analyte(s) may be pre-defined and stored in memory (e.g. for established workflows on standardized microfluidic devices).

At step 608, based at least in part of the information specifying the location of the reagent(s) and analyte(s) involved in the assay, the imaging module 164 automatically identifies at least one assay area $AA_x$. As discussed above, in some instances, the imaging module 164 automatically identifies a set of assay areas $AA_x$ (x=1 to n) corresponding to n different regions within the microfluidic device.

After the automatically-identified assay area(s) have been identified, the imaging module 164 communicates with the imaging device 194, at step 610, to obtain a set of n images $I_i$ (i=1 to n) of each assay area $AA_x$. After obtaining the set of images, and for each assay area $AA_x$, the imaging module 164 analyzes each image in the set of n images $I_i$ (i=1 to n) to determine, at step 612, the set of light intensity values and other properties corresponding to pixels within the automatically-identified assay area(s). The images may be transformed by digitization, background subtraction, excitation light field uniformity correction, hot pixel removal, image noise removal, quantitative image value to absolute light level transformation, and/or any other suitable transform prior to analysis. During the analysis, the imaging module 164 may iteratively refine or adjust the automatically-identified assay areas $AA_x$ based on set of light intensity values and/or other properties. For example, in some instances, the imaging module 164 may identify regions of the automatically-identified assay areas $AA_x$ that represent aberrant or outlier data, adjust the automatically-identified assay areas $AA_x$ to exclude these regions, and re-determine the set of light intensity values. For example, in some instances, the image module 164 may reject regions with strong but constant light levels or short-lived bright regions caused by micro-particles moving through the assay region. In some instances, the imaging module 164 can augment or extend the automatically-identified assay area(s) $AA_x$ to include additional pixels.

In one embodiment, based on the set of light intensity values generated for each image in the set of images, the imaging module 164, at step 614, determines the rate of change $\Delta_x$ of each assay area $AA_x$. The imaging module 164 uses the rate of change $\Delta_x$ of the assay area(s) $AA_x$ to generate a quantitative or absolute value for the assay. In instances where the imaging module 164 generates an absolute value, the imaging module 164 can compare the rate of change $\Delta_x$ of an assay area $AA_x$ to a pre-specified threshold $\Delta°$ to generate an absolute value specifying the presence or absence of an analyte. In instances where the imaging module 164 generates a relative value, the imaging module 164 can compare the rate of change of the assay area $AA_x$ to a calibration curve in order to determine a quantitative value for the assay. In these instances, the calibration curve is generated by calculating the rate of change of assay areas $AA_n$ corresponding to known concentrations of the analyte that is being measured in the assay.

In another embodiment, based on the set of light intensity values generated for each image in a set of images $I_i$, the imaging module 164 determines, at step 614, the rate of change $\Delta_x$ of the assay area $AA_x$ and the same values for a pre-defined set of neighboring pens (i.e. pens that are located proximal to the pen of interest in the microfluidic circuit). The imaging module 164 uses the rate of change $\Delta_x$ of the assay area $AA_x$ and the pre-defined set of neighbors to reject assay background noise and generate a quantitative or absolute value for the assay. In instances where the imaging module 164 generates an absolute value, the imaging module 164 can compare the rate of change $\Delta_x$ of the assay area $AA_x$ to a pre-specified threshold $\Delta°$ to generate an absolute value specifying the presence or absence of an analyte. In instances where the imaging module 164 generates a relative value, the imaging module 164 can compare the rate of change of the assay area $AA_x$ to a calibration curve in order to determine a quantitative value for the assay. The calibration curve is generated by determining the rate of change $\Delta_x$ of a set of assay areas $AA_x$ associated known quantities of the analyte (e.g. a series of pens, each with a fixed quantity of an analyte situated in the pen).

In another embodiment, based on the set of light intensity values generated for each image in the set of images, the imaging module 164 determines, at step 614, the absolute value of change $\Delta_x$ of the assay area $AA_x$ from the start of the assay to the end of the assay with a predetermined or auto determined time interval. The imaging module 164 uses the absolute value of change $\Delta_x$ of the assay area $AA_x$ to generate a quantitative or absolute value for the assay.

The methods of the invention can be used with a wide variety of different assays. In certain embodiments, the assay is an antigen detection assay. For example, biological micro-objects such as cells can be disposed in a microfluidic device, moved into sequestration pens (individually or otherwise), allowed to express antigens, and then screened for production of an antigen of interest. The screening can involve, for example, beads having an antigen-specific binding agent. Such beads can be disposed in a flow channel and/or or in a portion of a sequestration pen proximal to the flow channel, a labeled antigen-binding agent can be added, and an association between the labeled antigen-binding agent and the beads can be assessed in an automated manner, as discussed above. The labeled antigen-binding agent can bind to a different portion of the antigen of interest than the antigen-specific binding agent on the beads. Microfluidic antigen detection assays have been described in, for example, U.S. Patent Application Publication Nos. US2015/0151298 (Hobbs et al.) and US2015/0165436 (Chapman et al.), the contents of which are incorporated herein by reference in their entirety.

In certain embodiments, the invention further provides machine readable storage devices for storing non-transitory machine readable instructions for carrying out any of the foregoing methods. The machine readable instructions can further control the imaging device 194 used to obtain the images.

Although specific embodiments and applications of the invention have been described in this specification, these embodiments and applications are exemplary only, and many variations are possible.

What is claimed:

1. A method of detecting an assay-positive assay area within a microfluidic device comprising a microfluidic circuit having a sequestration pen and a flow channel configured to contain a fluidic medium, the method comprising automatically:

flowing a fluidic medium comprising a micro-object into the flow channel of the microfluidic device;

identifying an assay area based at least in part on a structural feature of the microfluidic circuit of the microfluidic device, wherein the structural feature is an opening from the sequestration pen to the flow channel;

collecting a set of digital images of the assay area;
calculating a rate of change of at least one parameter that characterizes a distribution of a set of light intensity values over the course of all or part of the assay based on the set of digital images of the identified assay area;
comparing the rate of change to a threshold value related to the at least one parameter; and
determining that the identified assay area is assay-positive if the rate of change is greater than the threshold value.

2. The method of claim 1, wherein the assay area is identified based at least in part on a dimension of the channel.

3. The method of claim 2, wherein the dimension of the channel includes a width or length of the channel.

4. The method of claim 1, wherein the assay area is identified based at least in part on a dimension of the sequestration pen.

5. The method of claim 4, wherein the dimension of the sequestration pen includes a width or a length of the sequestration pen.

6. The method of claim 1, wherein identifying the assay area further comprises determining a position of a biological micro-object within the sequestration pen.

7. The method of claim 1, wherein the assay area is identified based at least in part on whether the assay is a secretion assay or an antigen detection assay.

8. The method of claim 7, wherein the assay is a secretion assay and comprises a plurality of micro-objects disposed in the assay region area.

9. The method of claim 8, wherein the assay area is further configured to exclude regions of the assay area that represent abberant or outlier data.

10. The method of claim 8, wherein the assay augments or extends the automatically-identified assay areas to include additional pixels, dependent on the at least one parameter.

11. The method of claim 8, wherein the micro-objects comprise beads and an antigen-specific binding agent on the beads, and wherein the micro-objects are disposed in the flow channel and/or in a portion of the sequestration pen proximal to the flow channel.

12. The method of claim 11, further comprising flowing in a labeled antigen-binding agent with the micro-objects, wherein the labeled antigen-binding agent is configured to bind to a different portion of the antigen of interest than the antigen-specific binding agent on the beads.

13. The method of claim 1, wherein the assay area is identified based at least in part on a diffusion correlated property of a reagent or analyte used in the assay.

14. The method of claim 1, wherein the assay area is identified based at least in part on the location of a reagent or analyte that has been affixed to a portion of the sequestration pen or a portion of the channel.

15. The method of claim 14, further comprising affixing the reagent or analyte to the portion of the sequestration pen or the portion of the channel by using structured light to solidify a polymer network.

16. The method of claim 1, wherein the digital images are collected over time comprising a first time point and a second time point and with periodicity.

17. The method of claim 16, wherein a digital image of the set is collected every 3 to 5 minutes.

18. The method of claim 1, wherein each digital image of the set of digital images comprises a set of pixels, and wherein calculating the rate of change comprises determining a light intensity value or a set of light intensity values for the set of pixels or a subset of the set of pixels determined based on the identified assay area.

19. The method of claim 18, wherein determining a light intensity value for a pixel comprises subtracting a background level of light intensity from an observed level of light intensity.

20. The method of claim 19, wherein the background level of light intensity is measured for a given pixel prior to the start of the assay or at the beginning of the assay.

21. The method of claim 20, wherein the background level of light intensity is a light intensity value observed for a control area of the microfluidic device.

22. The method of claim 1, wherein the at least one parameter that characterizes the distribution of light intensity values comprises one or more of: the average light intensity value, the standard deviation of the light intensity value, a minimum light intensity value, and a maximum light intensity value determined for a set of pixels collected in each of the images in the set of images.

23. The method of claim 1, further comprising identifying a plurality of assay areas and wherein each image of the set of digital images shows a plurality of assay areas, and the threshold value for the at least one parameter comprises a sum of (i) an average rate of change for the distribution of values for the at least one parameter, wherein the distribution is obtained from the plurality of assay areas, and (ii) a standard deviation for the distribution of values obtained for each of the plurality of assay areas.

24. The method of claim 23, wherein the threshold is equal to the average rate of change plus 1.6 times the standard deviation for the distribution of the rates of change.

25. A non-transitory machine readable storage device for storing non-transitory machine readable instructions for carrying out the method of claim 1.

26. The method of claim 1, wherein the sequestration pen comprises an isolation region and a connection region configured to fluidically connect the isolation region to the flow channel.

27. The method of claim 1, wherein the microfluidic device comprises a plurality of sequestration pens and a plurality of corresponding assay areas.

28. The method of claim 1, wherein the sequestration pen opens laterally to the flow channel and the lateral orientation is configured to modulate exchange between fluid in the flow channel and the sequestration pen.

29. The method of claim 1, wherein the assay area is identified based on one or more of: the velocity of the fluidic medium, the viscosity of the fluidic medium, the presence of a polymerization agent within the fluidic medium, physical and chemical properties of analytes measured in the assay, the physical location of reagents or analytes used in the assay, the number of cells being assayed, or the amount of noise and background produced by analytes and/or reagents used in the assay.

* * * * *